US006886572B2

(12) United States Patent
Laughlin

(10) Patent No.: US 6,886,572 B2
(45) Date of Patent: May 3, 2005

(54) AUTOMATED SYSTEM FOR COATING THE HUMAN BODY: VIRTUAL MOTION

(75) Inventor: Thomas J. Laughlin, Grapevine, TX (US)

(73) Assignee: Laughlin Products, Inc., Grapevine, TX (US)

( * ) Notice: Subject to any disclaimer, the term of this patent is extended or adjusted under 35 U.S.C. 154(b) by 324 days.

(21) Appl. No.: 10/027,970

(22) Filed: Oct. 19, 2001

(65) Prior Publication Data

US 2002/0088475 A1 Jul. 11, 2002

Related U.S. Application Data

(63) Continuation-in-part of application No. 09/746,275, filed on Dec. 20, 2000, now Pat. No. 6,431,180, which is a continuation-in-part of application No. 09/663,023, filed on Sep. 15, 2000, now Pat. No. 6,298,862, which is a continuation-in-part of application No. 09/294,689, filed on Apr. 19, 1999, now Pat. No. 6,199,557, which is a continuation-in-part of application No. 08/946,764, filed on Oct. 8, 1997, now Pat. No. 5,922,333.

(60) Provisional application No. 60/241,770, filed on Oct. 20, 2000.

(51) Int. Cl.$^7$ ............................ A45D 44/00; A61K 6/00
(52) U.S. Cl. ....................................... 132/333; 424/401
(58) Field of Search ............................... 132/333, 200; 424/401, 59, 78.02, 78.03, 78.06

(56) References Cited

U.S. PATENT DOCUMENTS

| | | | |
|---|---|---|---|
| 870,766 A | 11/1907 | Eaton | |
| 1,262,638 A | 4/1918 | Class | |
| 1,982,509 A | 11/1934 | Frank | |
| 2,700,384 A | 1/1955 | Ivory | |
| 2,949,403 A | 8/1960 | Andreadis et al. | ............ 167/90 |
| 3,060,097 A | 10/1962 | Fellows | ...................... 167/91 |

(Continued)

FOREIGN PATENT DOCUMENTS

| | | | |
|---|---|---|---|
| BE | 814319 | 8/1974 | |
| DE | 141293 | 9/1901 | |
| DE | 36 05 807 | 2/1986 | |
| DE | 93 19 158.8 | 12/1993 | |
| DE | 9319158.8 | 3/1994 | |
| EP | 0 712 625 | 5/1996 | ............ A61K/7/42 |
| FR | 2725362 | 10/1994 | |
| WO | WO 94/12146 | 6/1994 | |
| WO | WO 00/54892 | 9/2000 | ........... B05B/15/12 |

OTHER PUBLICATIONS

Color Additives: Dihydroxyaceton, Federal Register, 38: No. 148, p. 20615, Aug. 2, 1973.

(Continued)

*Primary Examiner*—John J. Wilson
*Assistant Examiner*—Robyn Kieu Doan
(74) *Attorney, Agent, or Firm*—Michael A. O'Neil

(57) ABSTRACT

In a system for coating human skin, a chemical composition, such as a cosmetic or medical formulation, is uniformly coated over the entire body or selected parts of the body of the person being coated. The system includes atomization of the coating composition, containment of the atomized spray, and residual recovery which together yield a novel method for applying chemical compositions.

26 Claims, 31 Drawing Sheets

U.S. PATENT DOCUMENTS

| | | | | |
|---|---|---|---|---|
| 3,272,713 | A | 9/1966 | Runge | 167/90 |
| 3,856,934 | A | 12/1974 | Kligman | 424/62 |
| 3,868,950 | A | 3/1975 | Kato | 128/66 |
| 3,920,808 | A | 11/1975 | Fusaro | 424/59 |
| 3,932,151 | A | 1/1976 | Lau | 55/229 |
| 4,231,289 | A | 11/1980 | Domicent | 98/115 |
| 4,453,914 | A | 6/1984 | Huniu | 431/121 |
| 4,453,941 | A | 6/1984 | Jacobs | 8/424 |
| 4,749,130 | A | 6/1988 | Utzinger | 239/543 |
| 4,826,681 | A | 5/1989 | Jacquet et al. | 424/613 |
| 4,832,943 | A | 5/1989 | Grollier et al. | 424/59 |
| 4,874,412 | A | 10/1989 | Nowack | 55/385.1 |
| 5,073,996 | A | 12/1991 | Schinle | 4/601 |
| 5,089,269 | A | 2/1992 | Noda et al. | 424/456 |
| 5,102,660 | A | 4/1992 | Forestier et al. | 424/401 |
| 5,153,174 | A | 10/1992 | Band et al. | 514/12 |
| 5,232,688 | A | 8/1993 | Ziegler et al. | 424/59 |
| 5,268,166 | A | 12/1993 | Barnett et al. | 424/47 |
| 5,273,214 | A | 12/1993 | Huffstutler | 239/279 |
| 5,299,743 | A | 4/1994 | Sieth et al. | 239/248 |
| 5,302,378 | A | 4/1994 | Crotty et al. | 424/59 |
| 5,397,394 | A | 3/1995 | Orr | 118/634 |
| 5,456,211 | A | 10/1995 | Stevenson | 119/157 |
| 5,460,192 | A | 10/1995 | McClain | 132/333 |
| 5,494,674 | A | 2/1996 | Barnett et al. | 424/401 |
| 5,512,278 | A | 4/1996 | Mundschenk | 424/78.06 |
| 5,545,399 | A | 8/1996 | Lee et al. | 424/59 |
| 5,567,420 | A | 10/1996 | McEleney et al. | 424/60 |
| 5,603,923 | A | 2/1997 | Robinson et al. | 424/60 |
| 5,662,890 | A | 9/1997 | Punto et al. | 424/59 |
| 5,664,593 | A | 9/1997 | McClain | 132/333 |
| 5,700,452 | A | 12/1997 | Deckner et al. | 424/59 |
| 5,773,014 | A | 6/1998 | Perrier et al. | 424/401 |
| 5,880,314 | A | 3/1999 | Shinomiya et al. | 568/729 |
| 5,922,333 | A | 7/1999 | Laughlin | 424/401 |
| 6,117,118 | A | 9/2000 | Laughlin et al. | 604/290 |
| 6,199,557 | B1 * | 3/2001 | Laughlin | 132/333 |
| 6,214,322 | B1 | 4/2001 | Castro et al. | 424/59 |
| 6,231,837 | B1 | 5/2001 | Stroud et al. | 424/59 |
| 6,298,862 | B1 * | 10/2001 | Laughlin | 132/200 |
| 6,305,384 | B2 * | 10/2001 | Laughlin | 132/200 |
| 6,416,747 | B1 | 7/2002 | Laughlin | 424/59 |
| 6,421,180 | B1 | 7/2002 | Montgomery et al. | 359/618 |
| 6,431,180 | B2 * | 8/2002 | Laughlin | 132/200 |
| 6,439,243 | B2 * | 8/2002 | Laughlin | 132/200 |
| 6,443,164 | B1 | 9/2002 | Parker et al. | 132/333 |
| 6,446,635 | B2 * | 9/2002 | Laughlin | 132/200 |
| 6,468,508 | B1 | 10/2002 | Laughlin | 424/59 |
| 6,474,343 | B2 * | 11/2002 | Laughlin | 132/200 |
| 6,554,208 | B1 | 4/2003 | Venuto, Sr. | 239/207 |

OTHER PUBLICATIONS

Dihydroxyaceton–containing sunless or self–tanning lotions, Stanley B. Levy, Journal of the American Academy of Dermatology, 27: No. 6, pp. 989–993, 1992.

Formulating Effective Self–Tanners with DHA, T. Kurz, Cosmetics and Toiletries, 109: No. 11, pp. 55–60, 1994.

Non–Carcinogenicity of Dihydroxyaceton by Skin Painting, Frank J. Akin and Edward Marlowe, Journal of Environmenta Pathology and Toxicology, 5: No. 5, pp. 349–351, 1984.

Persistence of Skin Color and Fluroescence after Treatment with Dihydroxyaceton, J.A. Johnson & R.M. Fusaro, Dermatology 188: p. 247, 1994.

Spray Application Processes, Binks Training Division, TD49–2R–4, Aug. 1995.

Theory & Practice of Artificial Tanning Literature & Patent Survey, E. Futterer, Cosmetics and perfumes, 88: No. 8, pp. 31–33, 1973.

Fusaro et al. (1966), Sunlight protection in normal skin, *Archives of Dermatology*, vol. 93, pp. 106–111 (Jan. 1966).

Fusaro et al. (1970), Erythropoietic protoporphyria IV. Protection from sunlight. *Br. Med. J.*, vol. 1, pp. 730–731.

Fusaro et al. (1972). Protection against light sensitivity with dihydroxyacetone/naphthoquinone. *Int. J. Dermato*, vol. 11, pp. 67–70.

Fusaro et al. (1974). Photoprotection of patients sensitive to short and/or long ultraviolet light with dihydroxyacetone/naphthoquinone. *Dermatologica*, vol. 148, pp. 224–227.

Johnson et al. (1973). Protection against long ultraviolet light with dihydroxyacetone/naphthoquinone. *Dermatologica*, vol. 47, pp. 104–108.

Fusaro et al. (1971). Sunlight protection in patients with Chlorpromazine light sensitivity. *Int. J. Dermato*, vol. 10, pp. 198–200.

\* cited by examiner

```
SELECT COATING COMPOSITION
           ↓
   ATOMIZE COMPOSITION
           ↓
 CONTAIN ATOMIZED COMPOSITION
           ↓
DIRECT ATOMIZED COMPOSITION ONTO SKIN
           ↓
  CAPTURE RESIDUAL COMPOSITION
```

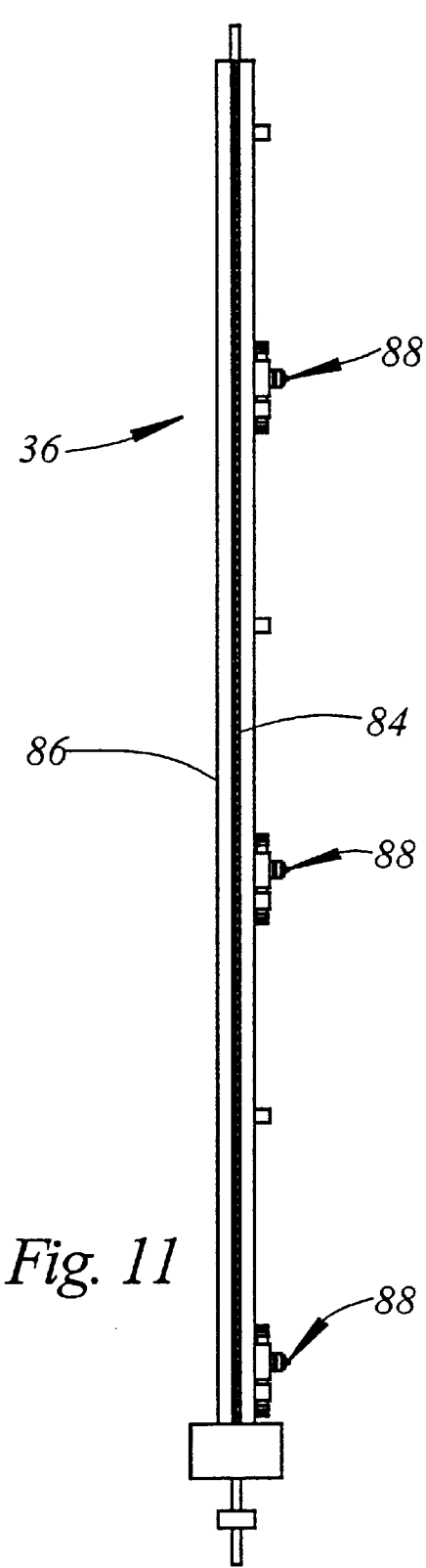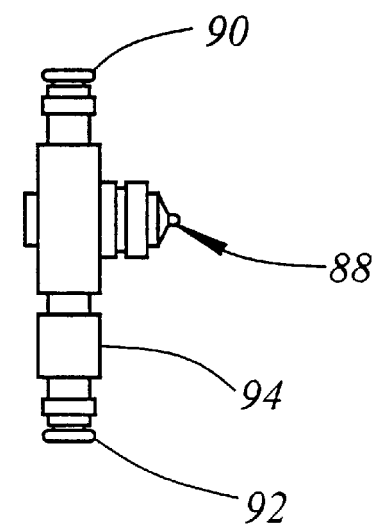
Fig. 11
Fig. 12

AUTOMATED SYSTEM FOR COATING THE HUMAN BODY: VIRTUAL MOTION

CROSS-REFERENCE TO RELATED APPLICATIONS

This application is a continuation-in-part of application Ser. No. 09/746,275 filed Dec. 20, 2000 now U.S. Pat. No. 6,431,180, which is a continuation-in-part of application Ser. No. 09/663,023 filed Sep. 15, 2000 now U.S. Pat. No. 6,298,862, which is a continuation-in-part of application Ser. No. 09/294,689, filed Apr. 19, 1999 now U.S. Pat. No. 6,199,557, which is a continuation-in-part of application Ser. No. 08/946,764, filed Oct. 8, 1997, now U.S. Pat. No. 5,922,333.

CLAIM OF PRIORITY

Applicant claims priority based on provisional patent application Ser. No. 60/241,770, filed Oct. 20, 2000.

TECHNICAL FIELD

The present invention relates generally to systems for automatically coating the human body or selected parts thereof with predetermined fluids which have been atomized into a fog or mist. More particularly, the invention relates to an automated system that controls the coverage pattern by using air currents to redirect the mist or fog thereby producing an effect similar to rotation or lateral movement of the atomization nozzle.

BACKGROUND OF THE INVENTION

The application of various fluids to all or selected parts of the human body has been known literally for centuries. However, despite the long-standing and widespread practice of coating the human body with various fluids, there has never been a successful way of automatically coating the human body. Therefore, prior to the present invention, it has been necessary to apply fluids to the body manually.

Manual application of fluids to the human body results in numerous disadvantages. First, it is almost impossible to uniformly coat the human body with fluids using manual application techniques. This is true even in the case of fluids that are provided in aerosol or spray form because such fluids must be rubbed in after application. Second, the application of fluids to certain parts of the human body, for example, the back, require the availability of an assistant in order that proper manual application can be attempted.

The foregoing difficulties are particularly apparent in the case of artificial tanning processes. Artificial tanning has been known for more than 40 years, with artificial tanning products appearing on the U.S. market as early as 1959. The two key types of tanning processes are by colorants and bronzers.

Tanning by colorants is based on the color reaction which occurs between components of the skin and the colorant. The most commonly used chemical for artificial tanning is dihydroxyacetone (DHA). It is widely used in commercial artificial tanning products, and is recognized as safe and effective by the U.S. Food and Drug Administration (FDA). DHA reacts solely with the stratum corneum. It interacts with amines, peptides and free amino acids to generate a Maillard reaction. The resulting products are cyclic and linear polymers that have a yellow or brown color.

Two common bronzers are juglone and lawsone. Both are naphthoquinones. When applied to skin, lawsone produces an orange hue and juglone produces a greenish-brown tan. They are sometimes used in combination with DHA to modify the color or hue of the tan or to intensify the color.

Numerous forms of artificial tanning products are now on the market. They include:

lotions,
creams,
gels,
oils,
sprays.

These products are mixtures of a chemically-active skin colorant or a bronzer with combinations of the following:

moisturizers,
preservatives,
anti-microbials,
thickeners,
solvents,
emulsifiers,
fragrances,
surfactants,
stabilizers,
sunscreens,
pH adjusters,
anti-caking agents,
ingredients to alter the color reaction.

Users of these products often experience significant problems associated with the current methods for applying artificial tanning formations to skin. These problems include the following.

If not properly dried, the formulation will streak or form blotches with time. The net result is a very nonuniform tan, with light or dark streaks or blotches.

Certain parts of the body will stain more intensely when the formulation is spread manually. This differential staining is due to enhanced absorption of certain skin tissue and the tendency of certain tissue to retain more formulation. The result is that as the formulation is being spread manually, certain tissue absorb or trap more formulation (e.g., the wrinkles in the elbows and knees and the dense tissue in the palms).

Most products designed for manual application require components such as thickeners and polymers, which often inhibit the efficacy of DHA.

Current formulations typically take about 20 minutes to dry to the touch, and about 1 hour before not transferring from skin to textiles.

Application of artificial tanning products is additionally complicated by the tendency of these formulations to stain materials containing amine molecules, including certain fabrics, certain types of carpet, and certain wall coverings and paint.

In spite of all of these problems, artificial tanning is becoming increasingly popular. It is apparent that a need exists for a superior application system which solves the foregoing problems.

There is also a need for a superior applications system for many other applications, including but not limited to:

self-tanning formulations,
sunscreens,
suntan lotions,
tanning accelerators,
sunburn treatments,
insect repellants, skin toners,
skin bleaches,
skin lighteners,
anti-microbial compositions,
moisturizers,
exfoliants,
nutriments or vitamins,
massage aids,
muscle relaxants,
skin treatment agents,
burn treatment agents,
decontamination agents,
cosmetics,
wrinkle treatments or removers.

There are specific and significant problems with the manual coating of each of these products. The artificial tanning application provides a good illustration of the types of problems normally encountered when manually coating with these products. Artificial tanning is also one of the most demanding applications in that uniformity of the coating is critical to assure uniform tanning.

SUMMARY OF THE INVENTION

The present invention comprises a system for automatically coating the human body, including a method of and apparatus for uniformly and rapidly coating all or selected parts of the human body. The system includes apparatus which atomizes (also referred to as aerosolization, nebulization, mist generation, fog generation or spray generation) a chemical composition and deposits it uniformly over all or selected parts of the human body. It is not necessary for the individual receiving the treatment nor anyone else to manually apply any of the formulation. Also, a containment system is provided which restrains and collects residue from the application process. The system can dispose of or recycle the materials used.

There are several major advantages resulting from the use of the invention:
Uniform application minimizes or eliminates streaking,
No assistant is required for applying the composition,
The entire skin surface receives the same exposure to the composition, so the uniformity of the coating is greatly enhanced over manual application,
The optimal formulation for atomization is very simple, and does not require the addition of components which may inhibit the efficacy of the applied material,
The application time can be as quick as a few seconds, and complete drying can occur in just a few minutes,
The containment system drastically reduces the unwanted environmental impact,
Multiple applications can be used to better control the amount of material applied per unit area, and additional substances can be applied in separate applications.

The invention may be practiced utilizing a unitary construction including both a coating chamber and apparatus for coating a person situated within the coating chamber. A door provides ingress to and egress from the coating chamber which is provided with strategically located spray discharging nozzles situated inside the chamber or in an adjacent area. A blower circulates air through the coating chamber to effect drying following the coating procedure and to aid in containment of excess spray. An air compressor supplies liquid for coating and compressed air for spraying the coating liquid to the nozzles situated within the coating chamber.

The invention may also be practiced utilizing a unitary construction including both a coating chamber and apparatus for coating a person situated within the coating chamber. A unique chamber has been invented to maximize tan quality, minimize user exposure to the mist, maximize application efficiency, and minimize the release of mist outside of the chamber.

An egress provides a means of entry to and exit from the coating chamber. In the preferred configuration, the egress is an unobstructed opening adequately large for an adult to enter and exit freely. The unique combination of booth and apparatus design result in little or no mist escaping from the booth during a coating session.

The solution is stored and dispensed in a novel cannister. The cannister, which is also a pressure vessel, has a double quick-disconnect fitting on both ends, so the cannister can be taken in and out of the system conveniently and cleaned by the system operator without any adjustments to the system or opening/closing of valves.

A recirculation system has been developed to assure uniform, steady state operation of the system even after extended periods of non-use. This system continuously recirculates the solution in the lines between the nozzles and the cannister.

Many of the embodiments of the invention disclosed herein employ spray discharging nozzles engineered for movement relative to the person being coated. However, the invention can also be practiced using virtual nozzle motion.

Virtual motion employs one or more sources of controlled air currents to selectively move the targeted coverage area relative to the coverage expected from a stationary nozzle. Multiple stationary nozzles and multiple air current sources can be strategically located relative to a person to be coated to effect a uniform coating over the entire body. By properly varying the intensity and volume of the air currents, the coating results can match and in some cases exceed the quality of coating obtained by actual nozzle motions.

REFERENCES

U.S. Patent Documents
U.S. Pat. No. 3,932,151 January 1976 Lau 55/229
U.S. Pat. No. 4,231,289 November 1980 Domicent 98/115
U.S. Pat. No. 5,268,166 December 1993 Barnett 424/047
Foreign Patent Documents
WO 94/12146 June 1994 PCT Int'l Appl.
Other Publications
Akins, F. J. and Marlowe, E., "Non-Carcinogenicity of Dihydroxyacetone by Skin Painting," Journal of Environmental Pathology and Toxicology, 5: No. 5, pp. 349–351 (1984).
Federal Register, "Color Additive Dihydroxyacetone" 38: No. 148, p. 21615, Aug. 2, 1973.
Futterer, E., "Theory and Practice of Artificial Tanning: Literature and Patent Survey," Cosmetics and Perfumes, 88: No. 8, pp. 31–33 (1973).
Johnson, J. A. and Fusaro, R. M., "Persistence of Skin Color and Fluorescence after Treatment with Dihydroxyacetone," Dermatology 188: pp. 247 (1994).
Kurz, T., "Formulating Effective Self-Tanners with DHA," Cosmetics and Toiletries, 109: No. 11, starting p. 55 (1994).
Levy, S. B., "Dihydroxyacetone-Containing Sunless or Self-tanning Lotions," Journal of the American Academy of Dermatology, 27: No.6, pp. 989–993 (1992).
"Spray Application Processes," BINKS training brochure TD49-2R-4, August, 1995, BINKS Manufacturing Company, Franklin, Ill.

BRIEF DESCRIPTION OF THE DRAWINGS

A more complete understanding of the invention may be had by reference to the following Detailed Description when taken in conjunction with accompanied Drawings, wherein:

FIG. 1 is a flow chart illustrating the invention;

FIG. 2 is a diagrammatic illustration of the system for automatically coating the human body of the present invention comprising the minimum requirements thereof;

FIG. 11 is an illustration of one of the spray columns of the apparatus of FIG. 9;

FIG. 12 is an enlarged view illustrating the nozzle assemblies utilized in the spray columns of the apparatus of FIG. 9;

DETAILED DESCRIPTION OF THE INVENTION

Figure 3:
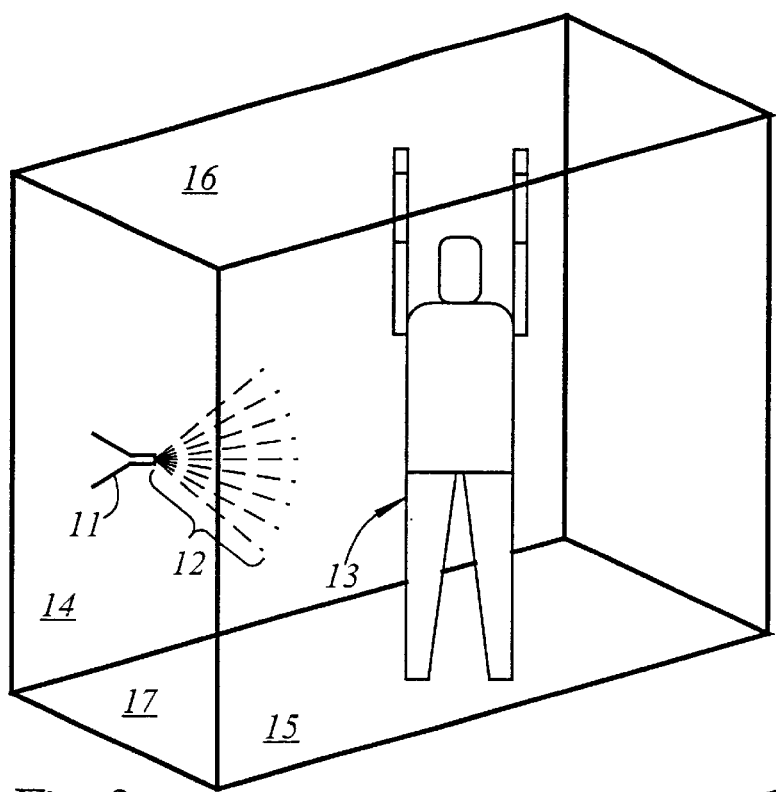
FIG. 3 is an illustration similar to FIG. 2 wherein the system of the present invention is further provided with containment apparatus.

Referring now to the Drawings, and particularly to FIG. 1, the system for automatically coating the human body of the present invention may comprise an automated coating system for numerous types of formulations, including but not limited to the application of:

self-tanning formulations,
sunscreens,
suntan lotions,
tanning accelerators,
sunburn treatments,
insect repellants,
skin toners,
skin bleaches,
skin lighteners,
anti-microbial compositions,
moisturizers,
exfoliants,
nutriments or vitamins,
massage aids,
muscle relaxants,
skin treatment agents,
burn treatment agents,
decontamination agents,
cosmetics,
wrinkle treatments or removers.

The first component of such a system is the chemical composition. The suitability of a composition for coating is strongly influenced by its viscosity, with the preferred viscosity being close to that of water (1 centipoise). Compositions with viscosities in the 1 to 10 centipoise range generally atomize well, and viscosities in the 10 to 100 range can be atomized, but the resulting spray is not as fine. Higher viscosities can be atomized, and will work, but the spray is not as fine. Most currently marketed compositions of the aforementioned applications can be made suitable for atomization either as is or with appropriate dilution.

By way of example, a more detailed description of functional compositions for use in practice of the invention will be based on artificial tanning compositions. Six such compositions are given in Compositions 1, 2, 3, 4, 5, and 6. Individuals skilled in this art can create other compositions.

| Ingredient | % |
|---|---|
| COMPOSITION 1 | |
| Dihydroxyacetone | 3.0 |
| Water | 97.0 |
| COMPOSITION 2 | |
| Dihydroxyacetone | 3.0 |
| Denatured Ethanol | 20.0 |
| Water | 77.0 |
| COMPOSITION 3 | |
| Dihydroxyacetone | 12.0 |
| Denature Ethanol | 20.0 |
| Water | 68.0 |
| COMPOSITION 4 | |
| Dihydroxyacetone | 10.0 |
| Commercial Sunless-Tanning Lotion | 15.0 |
| Water | 75.0 |
| COMPOSITION 5 | |
| Dihydroxyacetone | 9.0 |
| Commercial moisturizer | 20.0 |
| Citric acid | 0.3 |
| Commercial bath product | 0.6 |
| Bronzer | 6.0 |
| Water | 64.1 |

By way of example, a suitable commercial moisturizer would include Vaseline Brand Intensive Care Aloe and Naturals lotion (Chesebrough-Ponds, Greenwich, Conn.), and a suitable commercial bath product would include Vaseline Brand Intensive Care Foaming Creme Bath (Chesebrough-Ponds, Greenwich, Conn.). The bronzer is a combination of FD&C dyes that yield a golden brown color.

| COMPOSITION 6 | |
|---|---|
| Ingredient | % |
| Bronzer | 8.0 |
| Commercial moisturizer | 20.0 |
| Commercial bath product | 0.6 |
| Ethoxydiglycol | 2.0 |
| Water | 69.4 |

By way of example, a suitable commercial moisturizer would include Vaseline Brand Intensive Care Aloe and Naturals lotion (Chesebrough-Ponds, Greenwich, Conn.), and a suitable commercial bath product would include Vaseline Brand Intensive Care Foaming Creme Bath (Chesebrough-Ponds, Greenwich, Conn.). The bronzer is a combination of FD&C dyes that yield a golden brown color.

By way of example, suitable commercial preparations include Coppertone® Oil-Free Sunless Tanner (Schering-Plough, Memphis, Tenn.), Neutrogena® Glow Sunless Tanning Lotion for Face and Body (Neutrogena, Los Angeles, Calif.), and Kroger® Sunless Tanning Cream (Kroger, Cincinnati, Ohio).

Compositions 1, 2 and 3 are greatly simplified versions of the formulations now on the market or reported in the past. This simplification is possible due to the use of the present invention for applying compositions to skin. These simplified compositions have several advantages over more complex formulations, including:

faster drying, less potential inhibition of DHA efficacy, less potential for irritation from chemical components (because there are fewer components), less residue on the skin, less expensive, more environmentally friendly.

Compositions 4 and 5 illustrate how a commercial formulation not particularly well suited for atomization can be diluted, effectively atomized and uniformly coated on human skin. Similar dilutions of products representing the other aforementioned applications can be effectively atomized and coated on human skin.

There is no pH adjustment required for these compositions, although the pH can be adjusted to alter the hue of the resulting tan and to alter the dihydroxyacetone stability. The optimal tanning occurs with DHA at a pH of below 6.0, preferably with the solution at a pH of 3.0 to 4.0. Unbuffered DHA has a pH of about 5.5. The pH on the surface of human skin is also about 5.5. Nonetheless, these formulations can be used over a wide pH range, and buffers or pH adjusters can be added.

A preferred colorant is DHA. DHA is available from Rona (Hawthorne, N.Y.). It is effective, safe, and approved by the FDA for this application. The preferred DHA concentration is 0.5% to 20%, with a more preferred range of 3% to 15%, and a most preferred range of 5% to 12%.

Numerous other colorants can also be used. Those agents include, but are not limited to:

crotonaldehyde pyruvaldehyde glycolaldehyde glutaraldehyde otho-phthaldehyde sorbose fructose erythrulose methylvinylketone food coloring Various dyes and UV blocking agents can be covalently linked to the colorant or can be mixed into the composition with the colorant.

Bronzers can also be used in combination with or as an alternative to DHA. Bronzers which can be used include, but are not limited to, lawsone and juglone. Combinations of DHA and bronzers can also be used, and can be used to modify the resulting color (hue) and intensity of the tan. The preferred range for lawsone, juglone, and FD&C dyes is 0.5% to 10.0% with the more preferred range of 1.0% to 5.0%.

Composition 6 is an example of a formulation containing only bronzers (no DHA). The preferred range of FD&C dyes in commercially formulated liquid form (e.g., food coloring by Adams Extract Co., Austin, Tex.) is 1% to 50%, with a more preferred range of 4% to 12%. Ethoxydiglycol is added to enhance the penetration of the dyes into the skin, to reduce transfer to clothing, and to assist in the stabilization of the formulation.

The preferred ethoxydiglycol range is 1% to 20%, with a more preferred range of 2% to 10%.

Alcohol can be added to the composition to accelerate the rate of drying. Denatured ethanol (USP grade, commodity chemical) works well in this capacity. The preferred range for alcohol concentration is from 1.0% to 50.0%, with a more preferred range from 10.0% to 30.0%, and a most preferred concentration of 20.0%.

Other potential additives include:
moisturizers,
preservatives,
anti-microbials,
thickeners,
solvents,
emulsifiers,
fragrances,
stabilizers,
sunscreens,
surfactants,
pH adjusters,
anti-caking agents,
ingredients to alter the color reaction.

It typically requires about 100 ml of a 5.0% DHA composition to obtain a medium to dark tan over an entire adult body (about 2 square meters of skin). A single application of about 250 ml of a 9% dihydroxyacetone composition over an entire adult human body will result in a very dark tan. The exact amount of dihydroxyacetone required depends on the skin type and intensity of tan desired. The tan can last for about 2 to 7 days, but usually lasts for 3 to 4 days. Multiple applications will darken the tan.

The second component of the invention is the atomization of the composition. The required atomization can be obtained by a host of ways, most of which involve passing the composition through an orifice under pressure. Methods now used to atomize solutions include the use of the following systems:
air atomization
 siphon feed
 gravity feed
 pressure feed
  internal atomization
  external atomization
  low pressure low volume high volume low pressure
airless atomization
 pressurized through small orifices
 air-assisted
 air-assisted heated
electrostatic
 using charged particles
 heated charged particles
 high speed rotational atomizers
ultrasonic These forms of atomization are the basis for most methods of producing atomized sprays, including misting and nebulization.

Using a single airless sprayer with a tip orifice of 0.6 mm, with a circular spray pattern of 12 inches at 12 inches from the tip, and with a flow rate of approximately 400 ml/min. the entire body (excluding the bottom of the feet) of an average-sized person can be coated with solution in 5 to 15 seconds. In practice, the underside of the feet usually get slightly tanned also from exposure to small quantities of residual artificial tanning composition on the floor of the application area. The use of a single airless sprayer to apply a composition to human skin is illustrated in FIG. 2. In this figure and subsequent figures, 11 designates the orifice for atomization of the composition, 12 designates the atomized spray, and 13 designates the subject being sprayed. In this configuration, an operator must direct the flow of the spray. The configuration illustrated in FIG. 2 would also work for any of the other atomization methods aforementioned, and for any of the applications aforementioned. The preferred atomization method is the pressure-feed air-atomization system, with an internal or external atomization configuration.

For a person to be coated as illustrated in FIG. 2 with an artificial tanning composition (or any composition of the applications aforementioned), several precautions should be taken. First, the person should hold their breath during the application and during the time required for the spray to clear. If this process is done in an open area, the coating should take about 5 to 15 seconds and the clearing of residues should take 1 to 10 seconds. Thus, the person would need to hold their breath for 6 to 25 seconds. Alternatively, they could wear a filter over their mouth, have a filter inside of their mouth, or use a breathing tube. They can also wear nose plugs or filters. Second, the eyes should be protected even though most of these formulations are not likely to injure the eye. The simplest and most effective protection is to keep the eyes closed. Goggles or patches also work well, although they leave uncoated areas that must be subsequently coated manually. Next, precautions need to be taken if one wants to avoid the exposure of scalp hair. Scalp hair can be protected with a shower cap or any other similar protective covering impervious to the coating compositions. Also, hair can be coated with a water insoluble material such as petroleum jelly. Similar protection can be used to protect hair on any other parts of the body. Next, if atomization is from a single source, it is recommended that the person being coated turn while being coated, or that the coating apparatus be moved around the person being coated, or there be a combination of these movements. Finally, care must be taken that the nozzle remain at least several inches from the person being coated to prevent any possible injection of composition into the person. Generally, spray injection occurs at pressures greater than 500 psi with the person actually contacting the atomization orifice. The pressures here are less than 80 psi, and more typically 10 to 40 psi, and the person being coated should be a foot or more from the orifice.

The issue of what to wear during coating is usually of great concern to the person being coated. In the case of coating with artificial tanning solution, the selection of what to wear is a matter of preference for the person being coated. The subject can be coated nude, with underwear, with a bikini or a bathing suit, or with some form of pasties covering their private parts.

Figure 14:
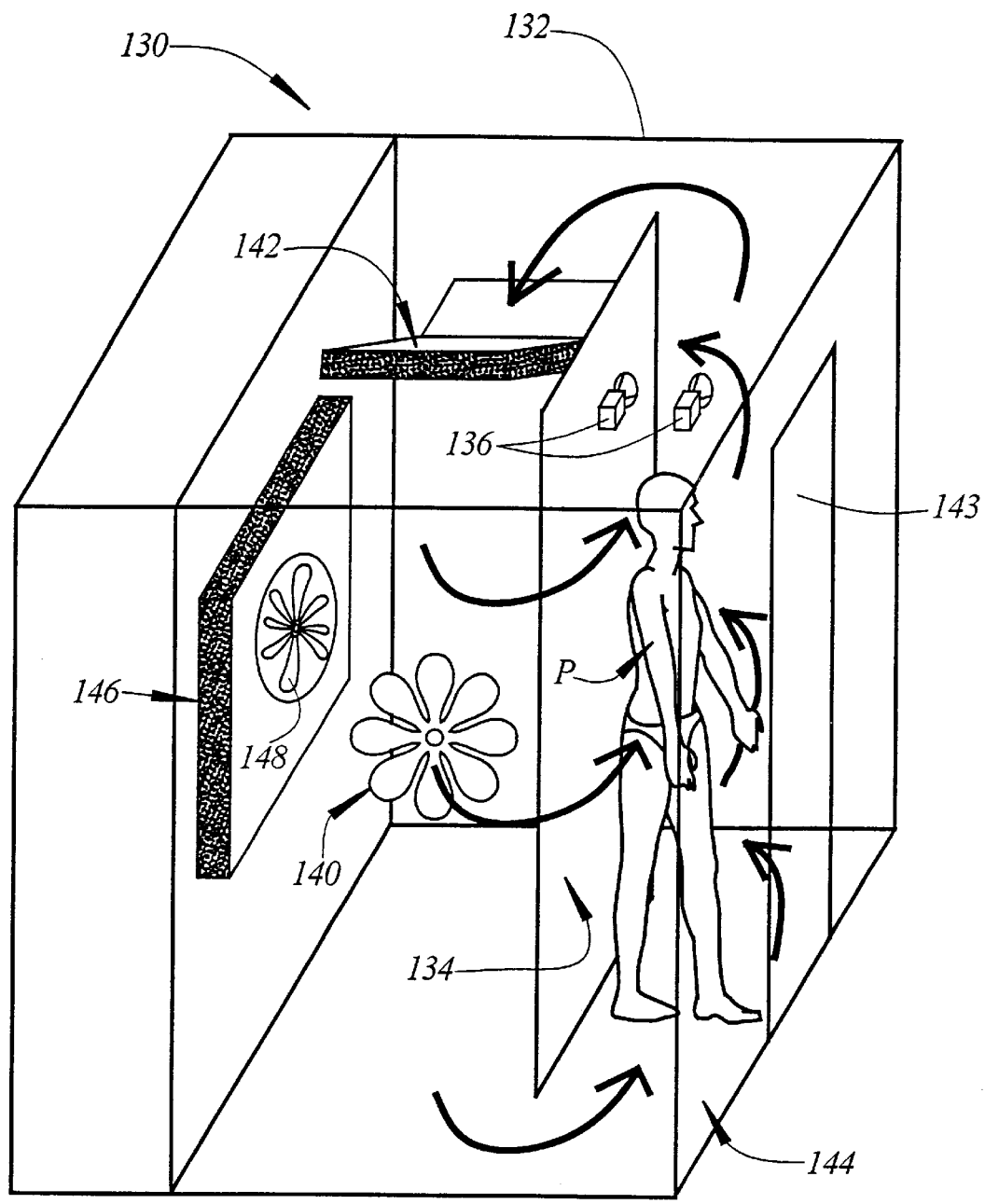
FIG. 14 is a diagrammatic illustration of a first variation of the apparatus of FIG. 13.
Figure 15:
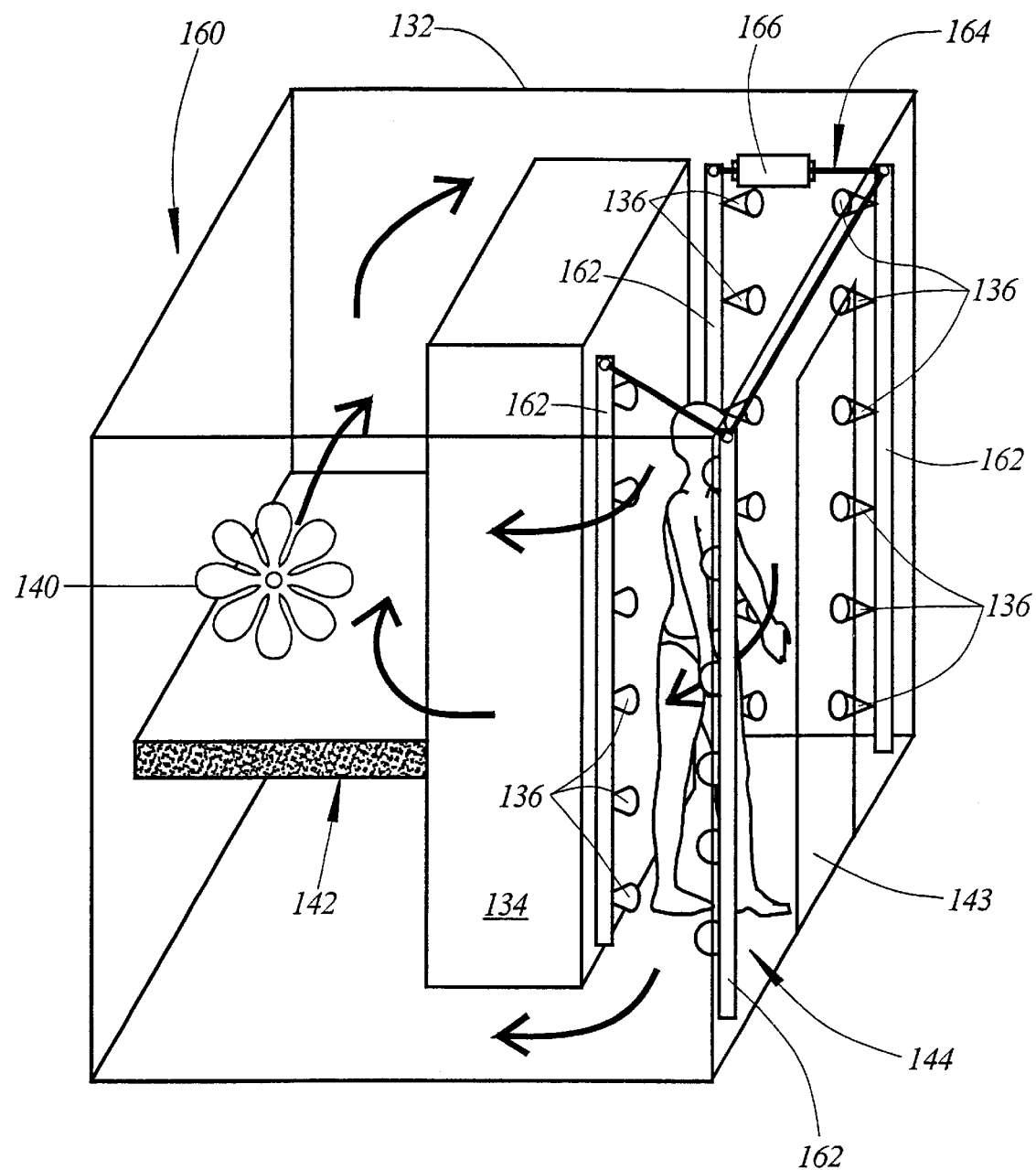
FIG. 15 is a diagrammatic illustration of a second variation of the apparatus of FIG. 13.

The third component of the invention is containment of the spray. Containment is illustrated in FIG. 3. In this figure and subsequent FIGS. 14 and 15 designate side panels and 16 and 17 designate the top and bottom panels, respectively. This type of containment is similar to the containment of spray paint using paint booths in automobile refinishing. Alternatively, spray containment can be obtained using electrostatic forces, where the atomized spray is charged and the residual charged spray is removed by activating charged collection plates. Of course, precautions must be taken so that the person being sprayed and the operator are isolated from the charged plates.

Containment of the spray is very important for several reasons. These reasons include but are not limited to:
- reducing waste,
- avoiding spray getting onto and staining items in the immediate surroundings,
- facilitating capture and recovery processes,
- better control of air flow,
- better control of temperature and humidity.

This type of containment facilitates the use of this invention in enclosed areas such as stores or medical facilities.

Figure 4:
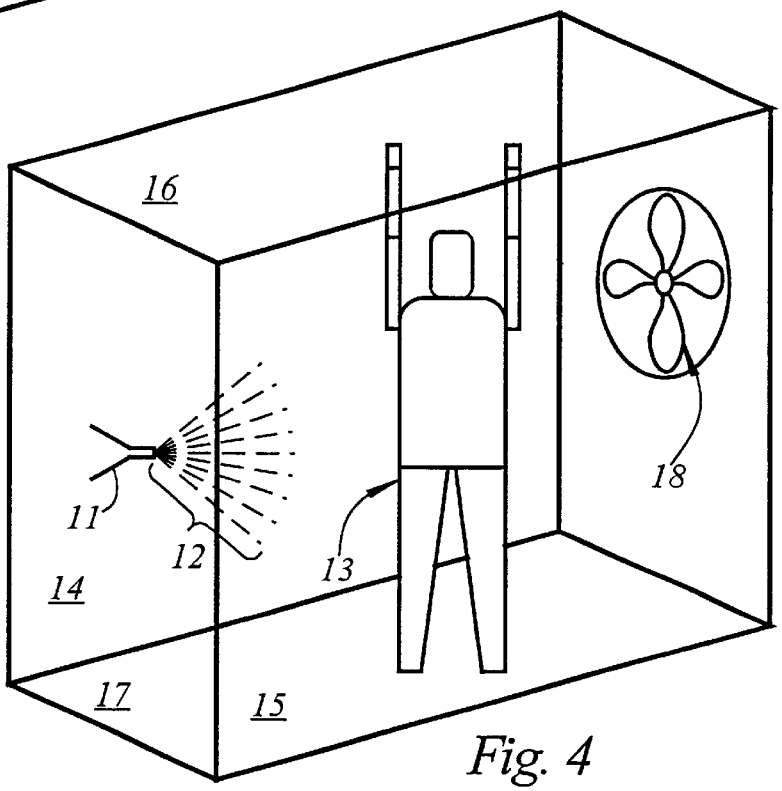
FIG. 4 is an illustration similar to FIG. 3 wherein the system of the present invention is further provided with an air ventilation apparatus.

Control of air and spray flow is very important to the quality of the skin coating. It is highly preferable to have an exhaust fan drawing the spray towards the person being coated, and the residual composition out of the booth. In FIG. 4 is shown the addition of an exhaust fan 18. The fan offers several significant advantages to the invention. These advantages include but are not limited to:
- better control of air flow
- shorter exposure to residue spray, requiring less time to hold breath or breathe through filter or air line
- faster drying of the coated composition on skin
- better quality coating The fan 18 should have a flow of 10 to 5000 cubic feet per minute per square foot of opening, preferably 50 to 1000 cubic feet per minute per square foot, and most preferably 100 to 400 cubic feet per minute per square foot. At flow rates of below 100 cubic feet per minute per square foot, the air movement is sufficient to guide the atomized spray through the containment area. At flow rates of 100 to 400 cubic feet per minute per square foot, the atomized spray is being actively drawn through the containment area and the application and drying process is enhanced. At rates above 400 cubic feet per minute per square foot, the atomized spray is being accelerated and the exhaust flow plays a much more prominent role in the application process. The flow rate of the air through the containment area is therefore a major parameter which can be varied to modify the characteristics of the coating of the artificial tanning composition to the skin. The drying time for the composition deposited on skin is also affected by flow rate, with drying time decreasing as flow rates increase. At rates above 100 cubic feet per minute per square foot, the drying time (to the point of no transfer to other surfaces upon contact) is less than 5 minutes.

At any flow rate above 10 cubic feet per minute per square foot, the residual atomized spray is completely removed from the containment area within one second. This rapid removal is important to minimize the time the person being tanned is exposed to spray and has the potential to inhale this spray. In the absence of this air flow, the residual spray lingers in the area for several minutes, and traces can be detected hours later. This vigorous flow also protects any individuals or operators near the atomizing orifices from back spray.

Figure 5:
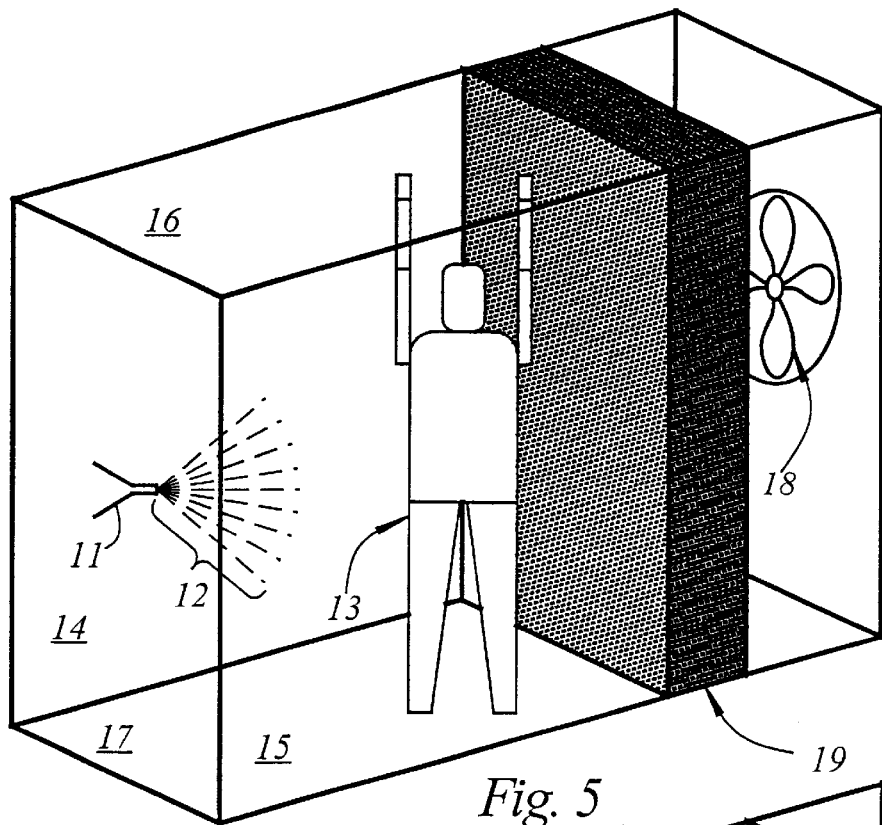
FIG. 5 is an illustration similar to FIG. 4 wherein the system of the present invention is further provided with collection apparatus for residual spray.

The final element of this invention is recovery, or filtering, of residual composition. This feature greatly enhances the utility of the invention because it allows the system to be self-contained in an indoor environment and promotes a more environmentally friendly process. Without a recovery system, there is a potential for the exhausted residue to stain anything it contacts. Also, there could be an accumulation of residue with time. One configuration of the recovery system is shown in FIG. 5. In this figure and subsequent figures, the recovery system or filter is denoted as 19. Recovery of both particulates and solvents is possible. Potential filters include a high-efficiency filter such as Binks' (Franklin Park, Ill.) Paint Pockets or Columbus Industries' (Ashville, Ohio) High-Capacity Supra Mini-Mesh, a form of a carbon filter, a water-wash filter, or an exchange-type resin. The efficiency of particulate and solvent removal should be greater than 99%. As an alternative to high-efficiency filtering, the spray residuals could be vented to the outside environment.

Figure 6:
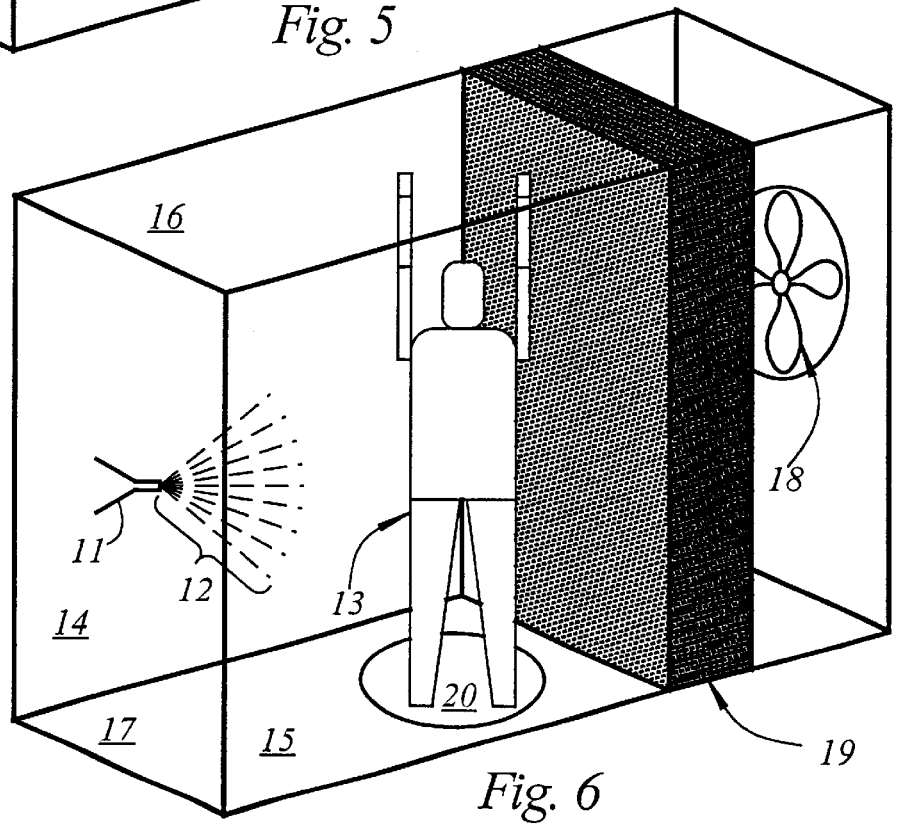
FIG. 6 is an illustration similar to FIG. 5 wherein the system of the present invention is further provided with apparatus to effect rotation of the human body being coated.
Figure 7:
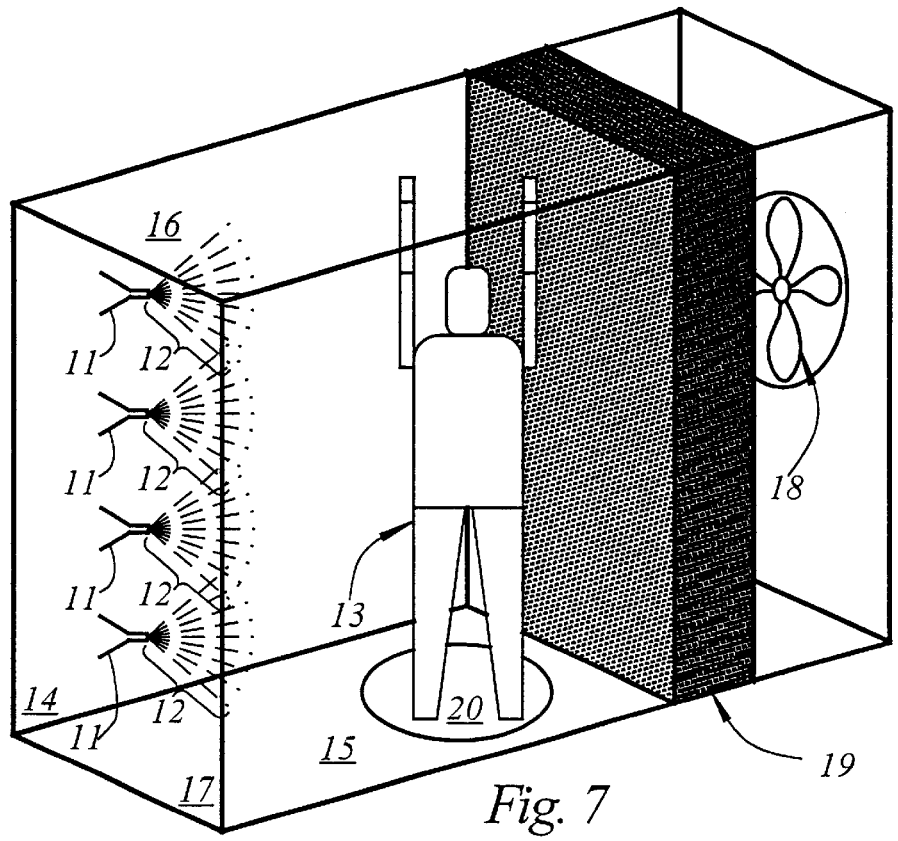
FIG. 7 is an illustration similar to FIG. 6 wherein the system of the present invention is further provided with multiple discharge nozzles.

Additional features adding to the utility of the invention are shown in FIG. 6 and FIG. 7. In FIG. 6 there is shown the addition of a motorized turntable 20. This turntable 20 will rotate the person being coated, eliminating rotation by the individual as a possible source of error or problems. It also is a major convenience for the person being coated. The preferred rate of rotation is in the range of 1 to 60 rpm, with a more preferred range of 5 to 20 rpm, with a most preferred rate of rotation of 12 rpm.

In FIG. 7 there is shown the use of multiple atomizing orifices. The use of multiple orifices facilitates the automation of this process, and reduces operator effort and potential error. It also reduces the time required to fully coat an individual. The typical round spray pattern is about 12 inches wide at 8 to 12 inches from the orifices, so a preferred spacing of multiple orifices will be 8 to 12 inches apart, but could be positioned from 1 to 48 inches apart. Fan patterns from wide-angle nozzles at 18 inches are typically 24 inches long and 9 inches wide. Using the preferred configuration, an individual can be coated in 5 seconds or less. In FIG. 7, the orifices are aligned in a vertical pattern. The coverage of more area at one time could also be obtained by rapidly moving one or more orifices along a track or by rapidly altering the angle of the orifice. Other patterns are possible, including combinations of vertical and horizontally aligned orifices. Orifices could also be aligned radially, with the subject being sprayed with orifices aligned from 0 to 360°. Another alignment is a horizontal ring containing orifices that surround the body. By vertically raising and lowering the horizontal ring, the entire body or selected parts of the body could be coated.

In an open environment, such as a beach or a park, a modified version of configuration illustrated in FIG. 7 could be used to rapidly coat an individual. It would even be possible to have a walk-through coating system. An atomized spray could be produced from multiple nozzles arranged in a single line (as shown in FIG. 7), in two single lines facing one another and about 36 to about 48 inches apart, or multiple lines of nozzles. The preferred configuration is multiple lines, with 4 lines being adequate. The atomized spray results in an area of intense atomized solution, which would coat an individual standing in that area. The residual spray would then be dissipated into the surrounding environment. A fan could be used to accelerate the removal of the residuals from the coating area.

Figure 8:
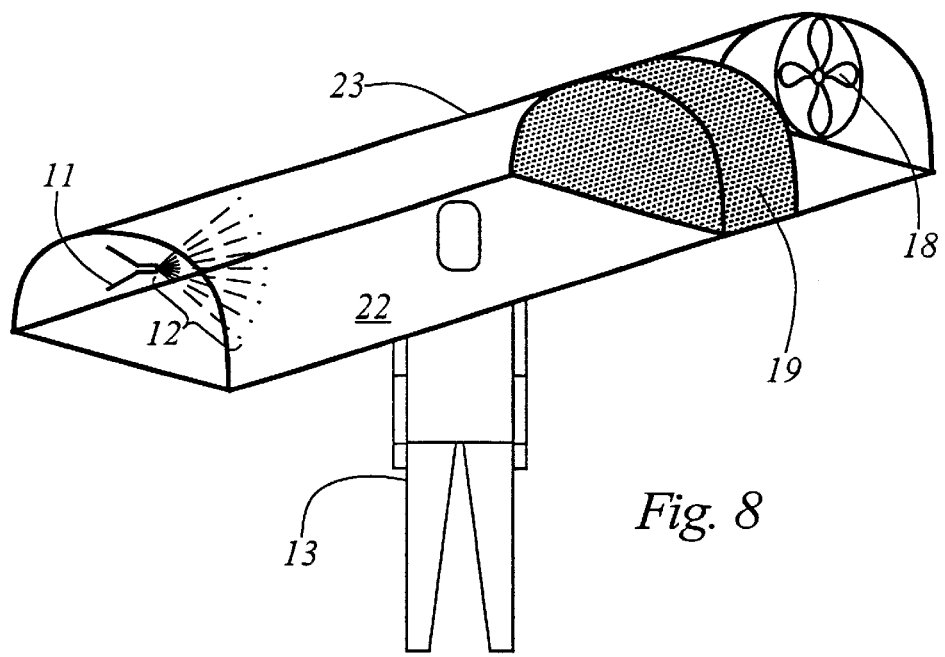
FIG. 8 is an illustration similar to FIG. 5 wherein the system of the present invention is adapted to the coating of a selected part of the human body.
Figure 9:
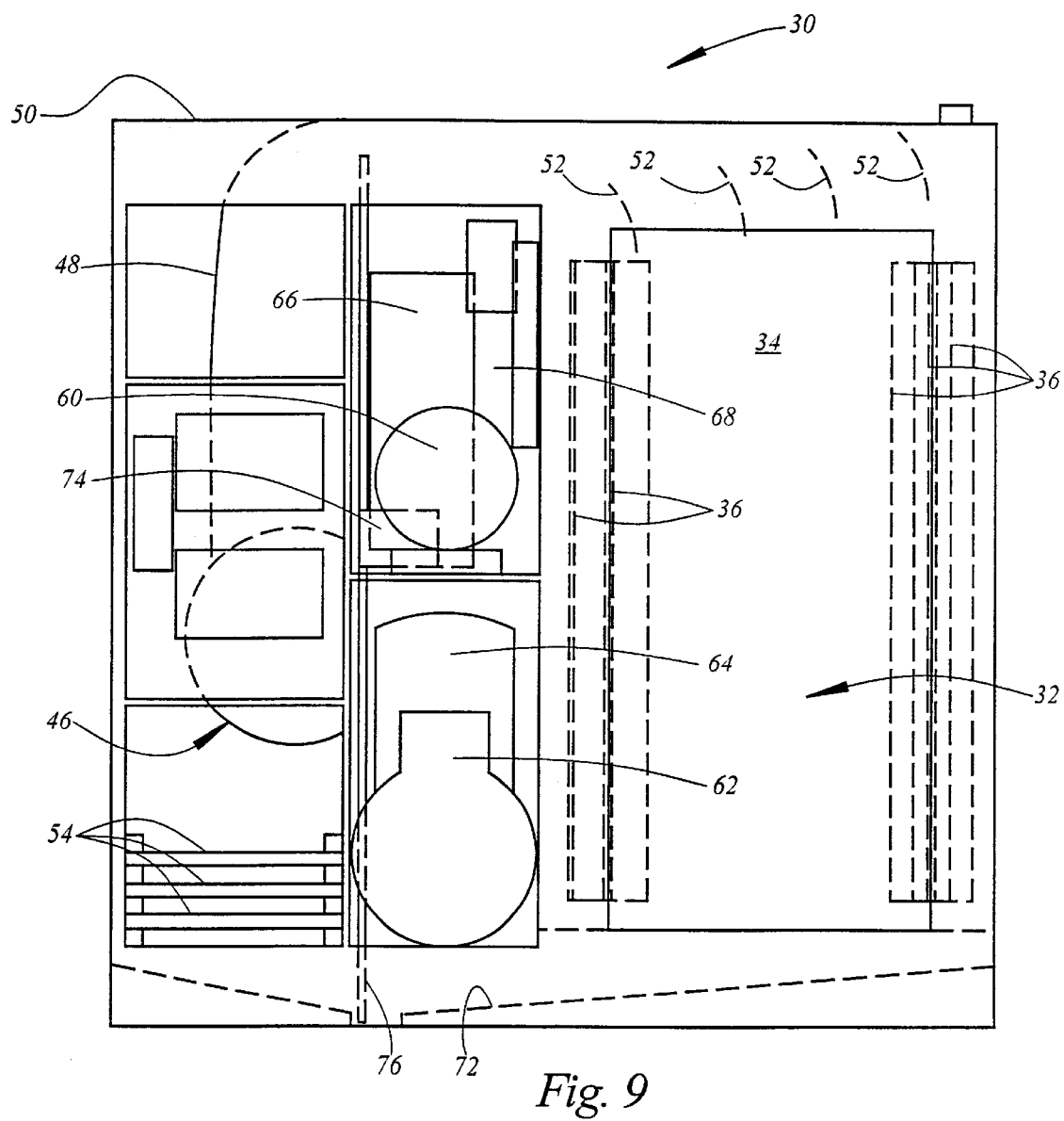
FIG. 9 is a front view of a first apparatus useful in the practice of the invention.

FIG. 8 illustrates how the system of the present invention can be used to tan a selected part of the body. In this case, just the face is being tanned. In this figure the bottom panel of the apparatus 22 contains an opening through which one can insert his or her head. The top panel 23 is arched. The high-efficiency filter is 19. The fan and back panel is 18. Alternately, the setup as shown in FIGS. 2–7 could be used to tan only a select part of the body by protecting the area not desired to be tanned with appropriate barrier apparel or by screens between the atomized spray and the regions of the skin not to be coated. The barrier apparel could be any material impervious to the atomized coating composition. For example, materials appropriate for use with the aforementioned coating compositions include vinyl, polyurethane, and latex rubber. The screens can be sheets composed of any material impervious to the atomized artificial tanning compositions, including most metals or plastics. A preferred screening material is foam with an impervious aluminum foil backing. The foam is aligned with the backing away from the atomizing orifice. The foam is preferred because it absorbs much of the atomized spray, reducing back deflection.

FIGS. 9, 10, 11, and 12 illustrate an apparatus which may be utilized in the practice of the invention. The apparatus 30 comprises a unitary construction which includes both a coating chamber 32 adapted to receive a person to be coated with a predetermined substance and various components utilized to effect spraying of the predetermined substance onto the person situated within the coating chamber 32.

Figure 10:
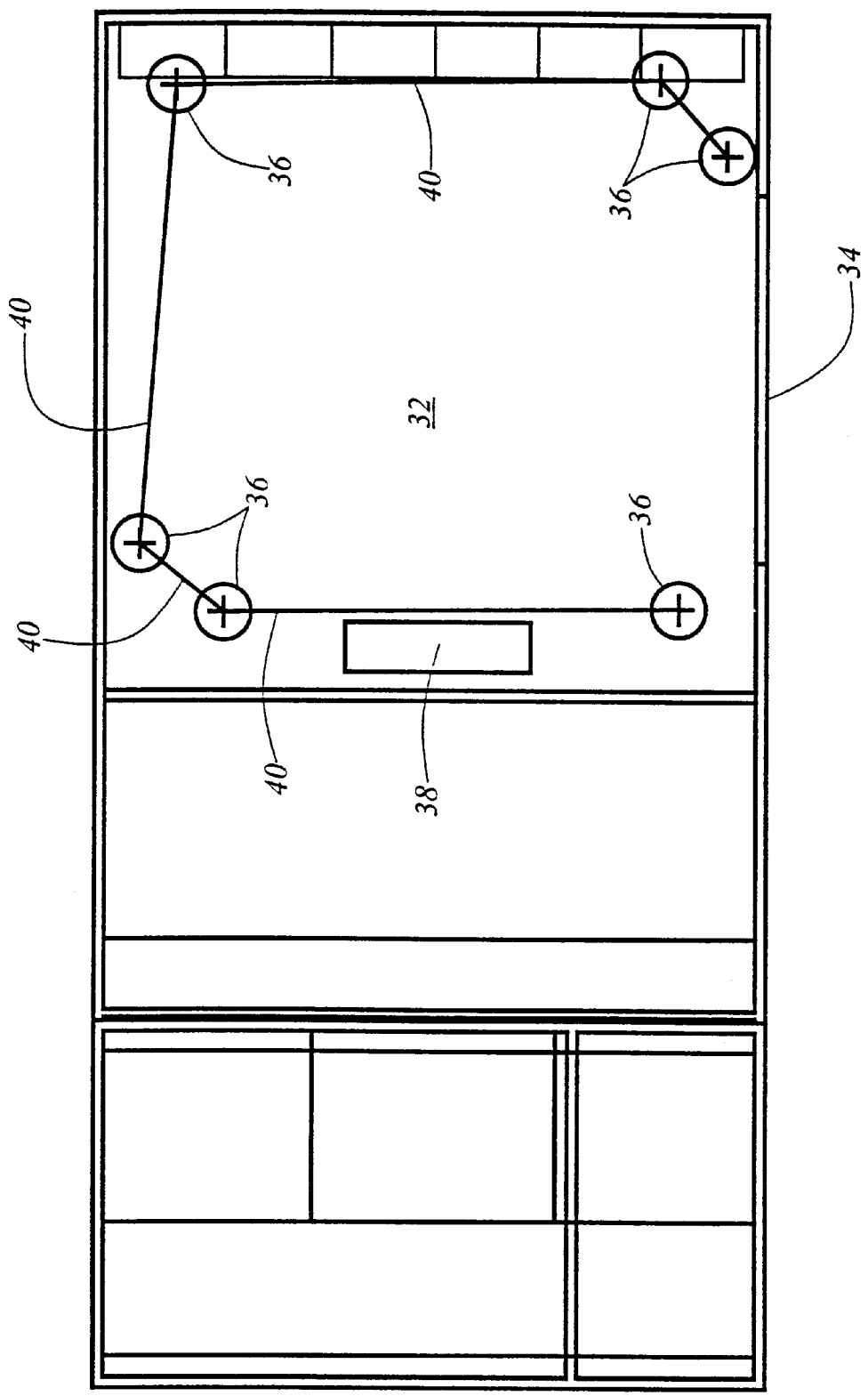
FIG. 10 is a top view of the apparatus of FIG. 9.

The coating chamber 32 includes a door 34 which affords ingress to and egress from the coating chamber. The coating chamber 32 is further provided with a plurality of spray columns 36. As is best shown in FIG. 10, the spray columns 36 are located at spaced apart points around the periphery of the chamber 32. Those skilled in the art will appreciate the fact that neither the number nor the precise location of the spray columns 36 is critical to the practice of the invention, and that other spray column arrangements may be utilized in the practice of the invention, if desired.

The spray columns 36 are preferably supported for pivotal movement through predetermined arcs under the action of a pneumatic cylinder 38. In this manner the predetermined material is discharged from the spray columns 36 in such a way as to assure uniform coating of the predetermined material on a person situated within the spray chamber 32. The pneumatic cylinder 38 is connected to the pivoting mechanism of each of the spray columns 36 through a plurality of links 40.

Referring again to FIG. 9, there is further included a blower 46 which directs a flow of air upwardly along an air guide 48 and then laterally along a top panel 50 into engagement with a plurality of baffles 52. The baffles 52 direct the air from the blower 46 downwardly through the coating chamber 32, whereby the flowing air effects drying of the sprayed material and aids in recovery of the sprayed material for reuse. From the coating chamber 32 the air is directed through a plurality of filters 54 and is returned to the blower 46.

The predetermined material which is to be coated onto a person situated within the coating chamber 32 is preferably provided in the form of a liquid which is received in a reservoir 60. The interior of the reservoir 60 is pressurized by compressed air which is received from an air compressor 62 through an air tank 64. Compressed air from the air compressor 62 in the tank 64 is also directed to an air tank 66 and to a manifold 68. The air tank 66 provides compressed air for operating the pneumatic cylinder (FIG. 10). The manifold 68 directs compressed air to the spray columns 36.

Ideally, all of the liquid from the reservoir 60 which is discharged from the spray columns 36 would be received on the body of the person within the coating chamber 32. In actual practice, it is not possible to obtain 100% efficiency in the coating procedure. Excess liquid which is discharged from the spray columns moves downwardly under the action of gravity onto a drain ramp 72. A drain pump 74 receives the excess liquid through a suction pipe 76 and delivers it to an appropriate drain.

Referring to FIGS. 11 and 12, each spray column 36 includes an inner tubular passageway 84 which receives liquid from the reservoir 60 under the action of compressed air supplied by the air compressor 62 through the tank 64 and an outer tubular passageway 86 which receives compressed air from the manifold 68. Each spray column 36 is provided with a plurality of nozzles 88. Each nozzle 88 receives compressed air from the outer tubular passageway 86 through a quick disconnect 90 and receives liquid from the inner tubular passageway 84 through a quick disconnect 92. A check valve 94 prevents reverse flow of liquid back through the quick disconnect 92.

Figure 13:
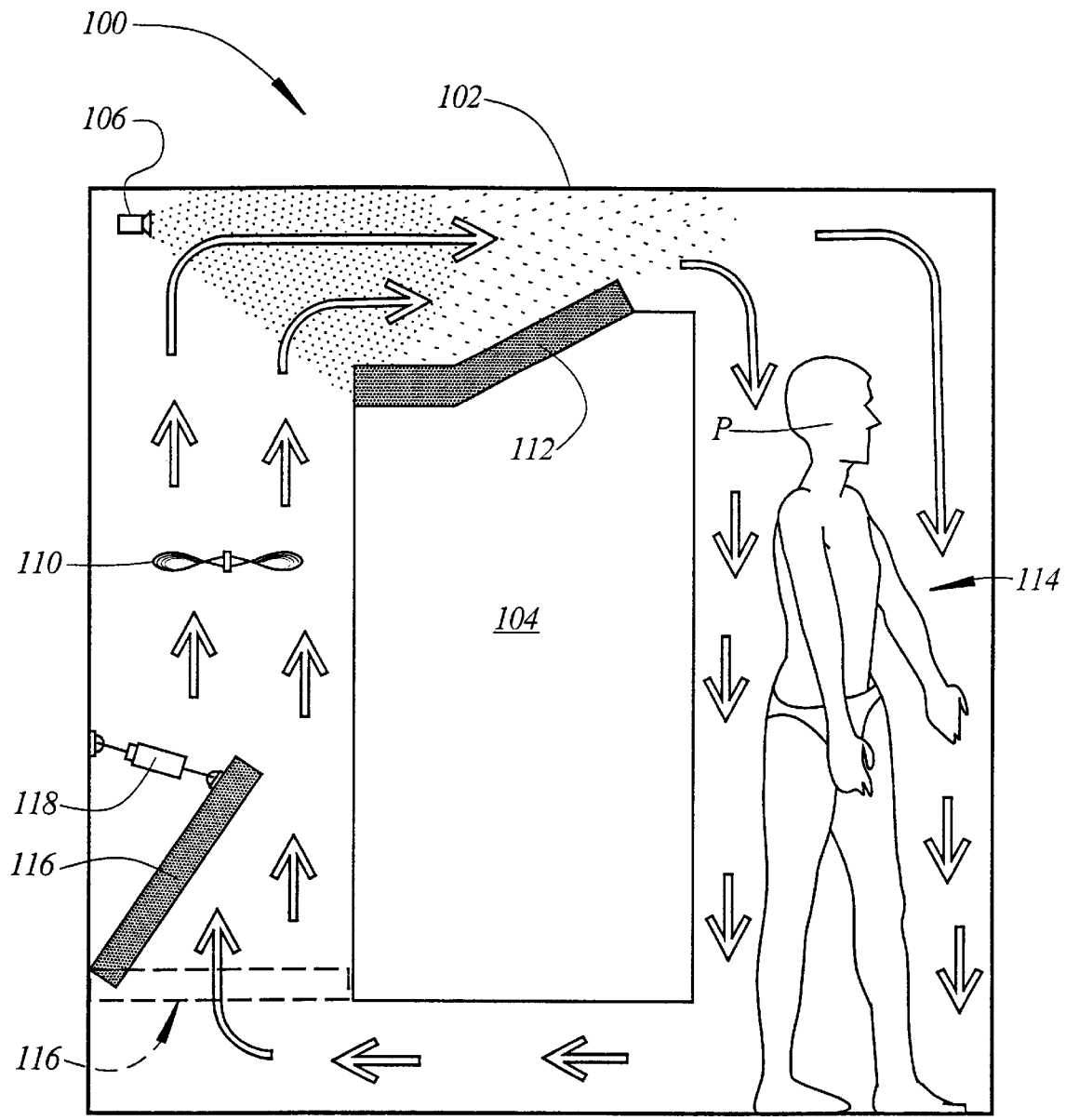
FIG. 13 is a diagrammatic illustration of a second apparatus useful in the practice of the invention.

Referring to FIG. 13, there is shown an apparatus for coating the human body 100 which may be utilized in the practice of the invention in lieu of the apparatus shown in FIGS. 9–12, inclusive. The apparatus 100 comprises an enclosure 102 having a barrier 104 disposed therein. One or more fogging nozzles 106 are utilized to generate a fog comprising a composition to be coated on all or part of the human body. As used herein, the term "fog" means liquid droplets which are small enough in size and light enough in weight to be entrained in and transported by moving air.

The fogging nozzles 106 are conventional in construction and operation. The fog generated by the fogging nozzles is similar to the insecticide fog which is generated by commercially available insect foggers. Other types and kinds of fogging devices are also well known and may be used in the practice of the invention.

The apparatus 100 further comprises a fan 110. The fan 110 causes air to flow within the enclosure 102 in a circular path around the barrier 104. The fog generated by the fogging nozzles 106 is entrained in the moving air and is transported thereby in the circular path as defined by the arrows in FIG. 13. Any droplets emanating from the fogging nozzles 106 which are too big and/or too heavy to be entrained in the moving air fall onto and are retained by an absorbent filter 112.

The chamber 102 defines a coating zone 114 situated on the opposite side of the barrier 104 from the fan 110. A person P to be coated stands within the coating zone 114. Upon operation of the fan 110 and the fogging nozzles 106, the fog comprising the composition to be coated envelopes the person P and is uniformly deposited on all or part of the body of the person P.

A filter 116 is normally positioned as shown in full lines in FIG. 13. This allows air and fog entrained therein to move around the circular path as identified by the arrows in FIG. 13 under the action of the fan 110. Whenever a particular coating operation has been completed, a fluid powered cylinder 118 is actuated to pivot the filter 116 into the position illustrated in dashed lines in FIG. 13. The fan 110 continues to operate thereby causing the fog entrained in the moving air to be captured by the filter 116. After all of the fog has been captured by the filter 116, the apparatus 100 is ready for a subsequent coating operation.

Referring to FIG. 14, there is shown an apparatus for coating all or part of the human body 130 comprising the variation of the apparatus 100 shown in FIG. 13 and described hereinabove in connection therewith. The apparatus 130 comprises a housing 132 having a barrier 134 disposed therein. One or more fogging nozzles 136 are positioned in the upper portion of the housing 132. In use, the fogging nozzles 136 function to generate a fog comprising a composition to be coated on all or part of the human body.

A fan is positioned within the housing 132 and functions to cause air to flow through the housing 132 and around the barrier 134 in the direction of the arrows shown in FIG. 14. The fog comprising the composition to be coated which is generated by the fogging nozzles 136 is entrained in the moving air and is transported thereby through the housing 132 in the direction of the arrows. Any droplets emanating from the fogging nozzles 136 which are too large and/or too heavy for entrainment in the moving air are captured by an absorbent filter 142.

A door 143 provides access to a coating zone 144 situated within the housing 132. The fog comprising the composition to be coated passes through the coating zone 114 under the action of the fan 140, thereby completely enveloping the body of a person P situated within the coating zone. In this manner, the composition comprising the fog generated by the fogging nozzles 136 is uniformly distributed over all or part of the body of the person P situated within the coating zone 144.

At the end of a coating session, excess fog, that is, coating composition which was not received on the body of the person P, is directed into an absorbent filter 146 under the action of an exhaust fan 148. After the interior of the housing 132 has been cleared of excess coating composition, the apparatus 130 is ready for a subsequent coating operation.

Referring to FIG. 15, there is shown an apparatus for coating all or part of a human body 160. The apparatus 160 incorporates numerous component parts which are substantially identical in construction and function to component parts of the apparatus 130 illustrated in FIG. 14 and described hereinabove in conjunction therewith. Such identical component parts are designated in FIG. 15 with the same reference numerals utilized above in the description of the apparatus 130.

The apparatus 160 differs from the apparatus 130 in that the fogging nozzles 136 of the apparatus 160 are mounted on vertically oriented tubular columns 162. The columns 162 are supported for pivotal movement about vertical axes, and are interconnected by a linkage 164. The linkage 164 is operated by an actuator 166 which functions to continuously pivot the columns 162 and the fogging nozzles 136 carried thereby back and forth about their respective vertical axes. Thus, the actuator 166 and the linkage 164 operate similar to the cylinder 38 and the links 40 of FIG. 10.

In the operation of the apparatus 160, the fan 140 circulates air through the housing 132 and around the barrier 134 in the direction of the arrows of FIG. 15. The fogging nozzles 136 function to generate a fog comprising a composition to be coated on all or part of the human body. The fog is entrained in the moving air and is transported thereby through the housing 132.

As the fogging nozzles 136 function to generate a fog from the coating composition, the fogging nozzles 136 are pivoted in horizontal planes by the actuator 166, the linkage 164, and the vertically oriented tubular columns 162. In this manner the initial distribution of the fog generated by the fogging nozzles 136 is turbulent rather than linear. Turbulence of the fog within the coating zone 144 of the housing 132 is beneficial in that it further assures a uniform distribution of the coating composition over all or part of the body of a person situated within the coating chamber.

Referring now to FIGS. 16–25, inclusive, there is shown an apparatus for automatically coating the human body 170 which may be utilized in the practice of the invention in lieu of the various apparatus illustrated in FIGS. 2–15, inclusive, and described hereinabove in conjunction therewith. The apparatus 170 includes a generally rectangular housing 172 including opposed side walls 174, a back wall 176, a top assembly 178, and a bottom assembly 180.

The housing 172 further defines a mist discharge and confinement zone 186 which is situated at the opposite end of the housing 172 from the back wall 176. The mist discharge and confinement zone 186 includes a floor 188 comprising part of the bottom assembly 180. The floor 188 in turn comprises an area 190 upon which a person P is located during the coating operation.

During operation of the apparatus 170 to effect coating the body of the person P situated within the area 190, mist is discharged from a mist discharge column 196. The mist discharge column 196 is supported from an arm 198 which is in turn supported on the top assembly 178 for pivotal movement about an axis 200. This causes the mist discharge column 196 to move back and forth along a shallow arc 202. The length of the arm 198, that is, the distance from the axis 200 to the mist discharge column 196, is sufficiently long that the arc 202 mimics the curves that define the front, back, and sides of the human body.

The mist discharge and confinement zone 186 further comprises arcuate panels 206 situated adjacent the side walls 174. A plurality of filter panels 208 extend between the arcuate panels 206 and define an array extending continuously between the top assembly 178 and the bottom assembly 180. A filter (not shown in FIG. 16) is situated behind each filter panel 208 and a suction fan (also not shown in FIG. 16) is situated behind each filter. The suction fans situated behind the filter panels 208 function to draw mist discharged from the mist discharge column 196 toward, onto, around, and past a person P situated within the area 190. In this manner excess mist, that is mist which is not coated onto the body of the person P, is contained and is not allowed to escape from the apparatus 170. It will be noted in this regard that the end of the housing 172 opposite the end 176 is entirely open and does not require the use of doors or other closure apparatus to contain the mist discharged from the mist discharge column 196.

The ability to retain the mist in the apparatus 170 without the use of doors was a surprising discovery. This retention is possible only with the presence of a front shield that is at least 75% of the width of the width of the confinement zone 186. With the mist being generated for the entire arc 202, the large volume of atomization air required results in a significant back flow of mist. Even at high air flows through the filters, the filtration system cannot handle this high quantity of air and mist. In the absence of a front shield, that mist escapes from the containment area. In the presence of the front shield, the air flow pattern is drastically altered. As the mist entrapped in the air flow approaches the front of the confinement zone 186, the mist is forced to move either towards the opening or towards the rear of the moving mist discharge column 196. The atomized air from the column produces a high-pressure zone in front of the nozzles, and a low-pressure zone behind the column. The mist therefore moves towards the low pressure zone behind the column, and is effectively recirculated. Little or no mist escapes through the opening.

Referring now to FIGS. 17 and 18, the construction of the top assembly 178 of the apparatus for automatically coating the human body 170 is shown in greater detail. The top assembly 178 includes side panels 218, an end panel 220, and a horizontally disposed panel 222 extending between the side panels 218. The side panels 218 and the horizontally disposed panel 222 may comprise multiple component parts which are reinforced by connectors 223.

The arm 198 comprises opposed channel members 224 which are secured one to the other by a plurality of fasteners 226. The channel members 224 are pivotally secured to the end panel 220 by a hinge 228 which defines the axis 200. The distal ends of the channels members 224 are received in a tube 230. A support plate 232 is mounted on the horizontally disposed panel 222 and is situated beneath the tube 230. As is best shown in FIG. 18, a pair of rollers 234 are supported on the tube 230 and engage the support plate 232. In this manner, the arm 198 is supported for pivotal movement about the axis 200.

Figure 17:
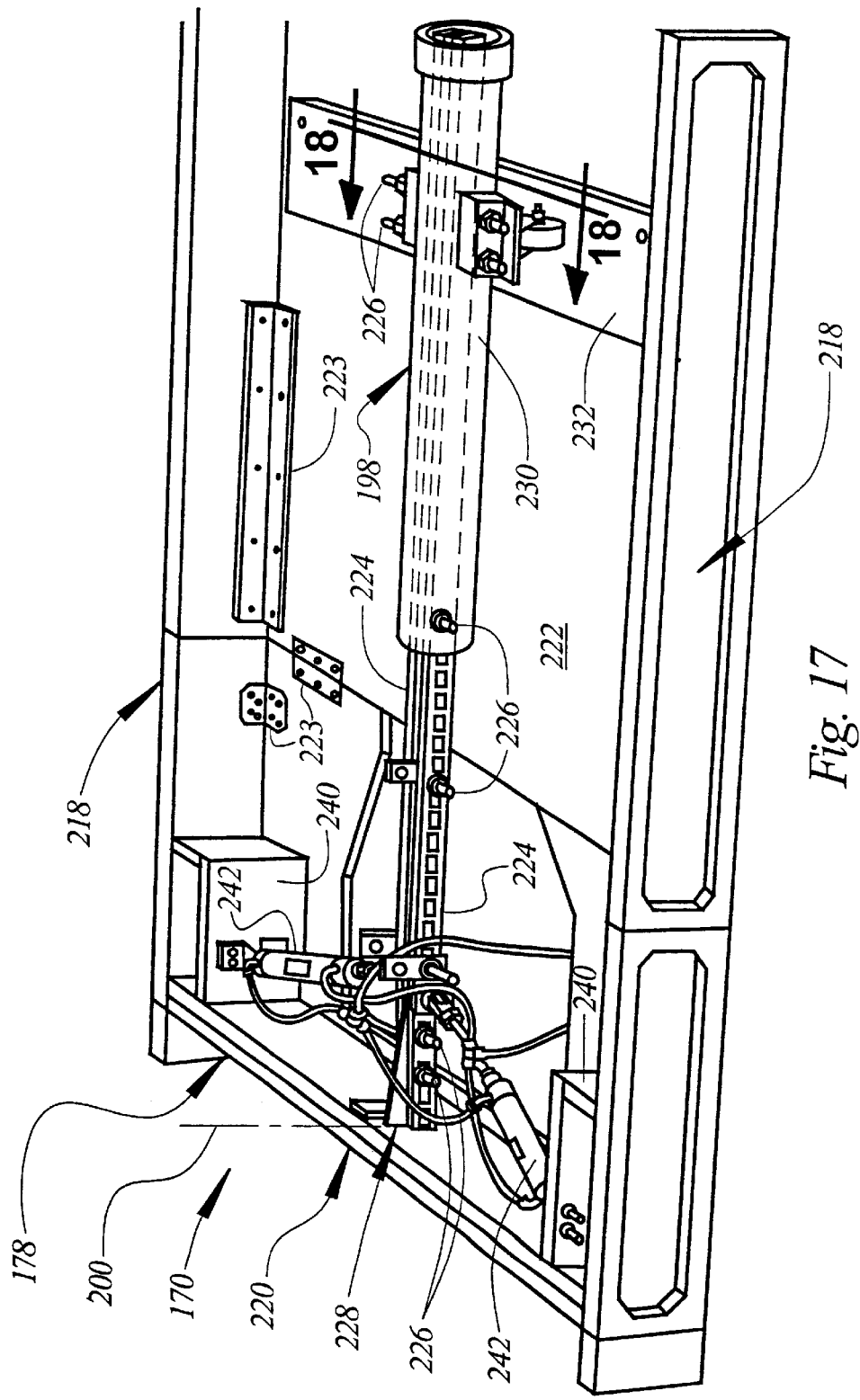
FIG. 17 is a perspective view illustrating component parts of the apparatus of FIG. 16.
Figure 18:
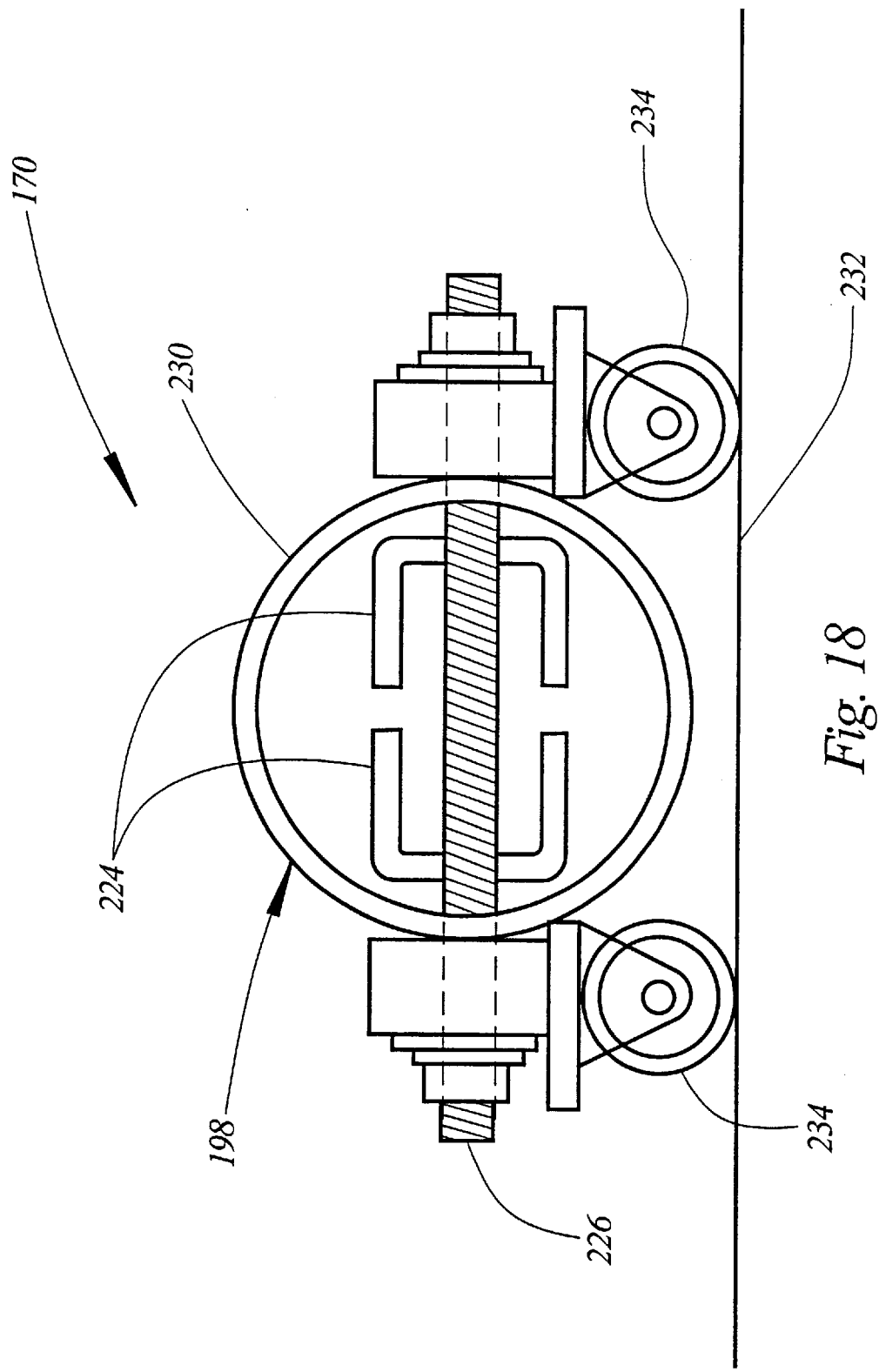
FIG. 18 is a partial perspective view taken along the line 18-17 in FIG. 17.

Referring again to FIG. 17, spacers 240 extend between the side panels 218 and the end panel 220 of the top assembly 178. Fluid powered cylinders 242 are connected between the spacers 240 and the channels 224 comprising the arm 198. Upon actuation, the fluid powered cylinders 242 effect pivotal movement of the arm 198 about the axis 200. As will be understood, during pivotal movement of the arm 198 above the axis 200 the rollers 234 move back and forth along the support plate 232.

Figure 19:
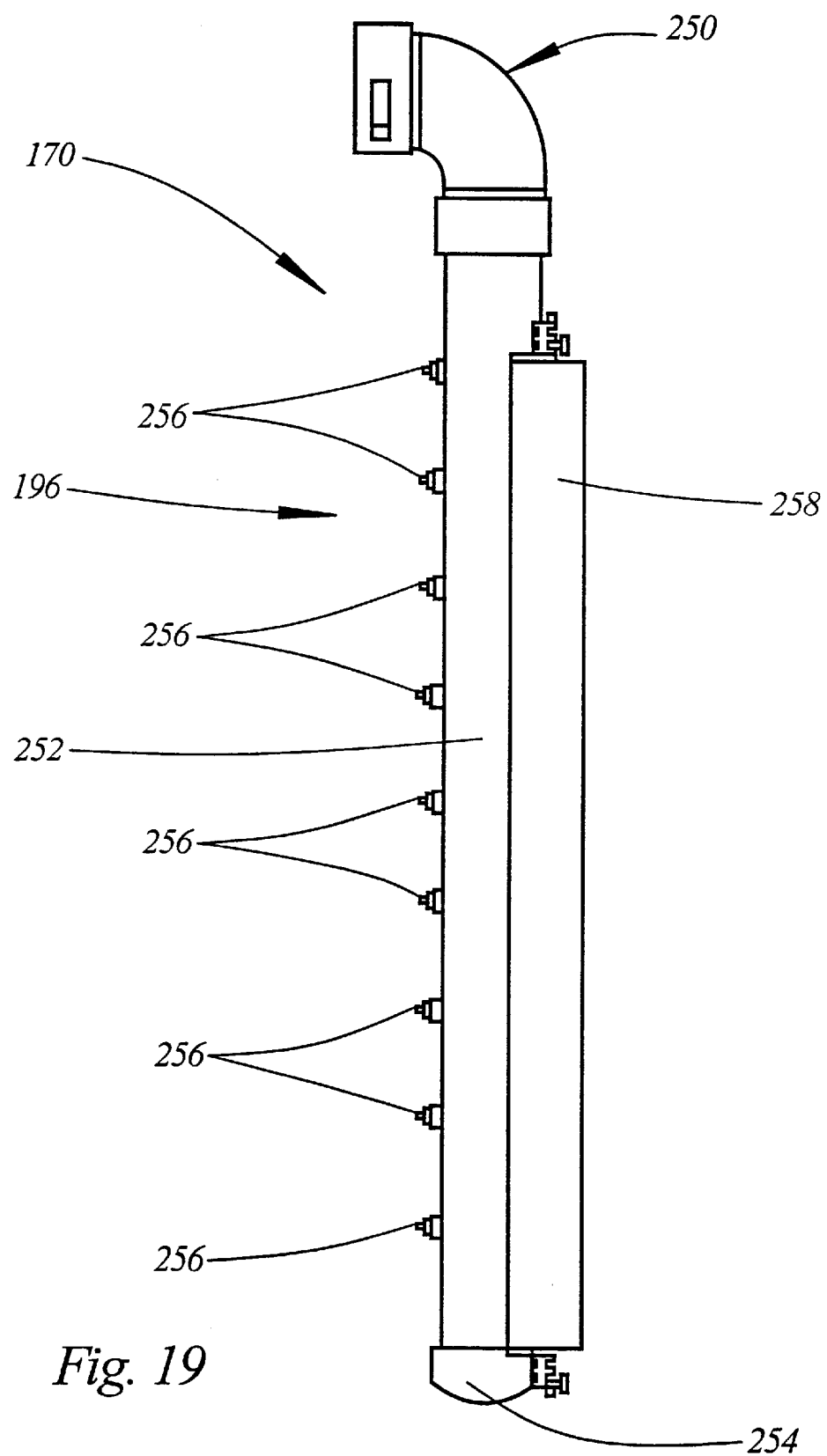
FIG. 19 is a partial side view further illustrating the apparatus of FIG. 16.

The construction of the mist discharge column 196 is further illustrated in FIG. 19. The upper end of the mist discharge column 196 comprises an elbow 250 which receives the distal end of the tube 230 comprising the arm 198 and is secured thereto by suitable fasteners (not shown). A tube 252 is in turn secured to the elbow 250 and extends vertically downwardly therefrom to a bottom member 254. A hingedly supported cover panel 258 provides access to the interior of the column and affords additional space for housing components. A plurality of mist discharge nozzles 256 are mounted on the mist discharge column 196 to effect the discharge of mist therefrom. The mist discharge nozzles are actuated by a spray column which is contained within the cover panel 258. A single solenoid controls air flow to all of the nozzles. Air flow must be present prior to and after liquid flow to assume a high quality mist. Each nozzle has a dedicated solenoid, located as close to the nozzles as possible, which controls the flow of liquid through the nozzle.

The operation of the nozzles 256 comprising the mist discharge column 196 differs somewhat from the operation of the spray column 36 in that the nozzles 256 of the mist discharge column 196 are arranged in at least two zones each comprising a plurality of nozzles with the operation of the nozzles comprising each zone being controlled by the solenoids individual to the nozzles of the zone. The two zones of nozzles may be operated simultaneously, sequentially, or independently depending upon the requirements of particular applications of the invention. Those skilled in the art will appreciate the fact that the nozzles 256 of the mist discharge column 196 may be segregated into three or more zones, if desired.

Figure 20:
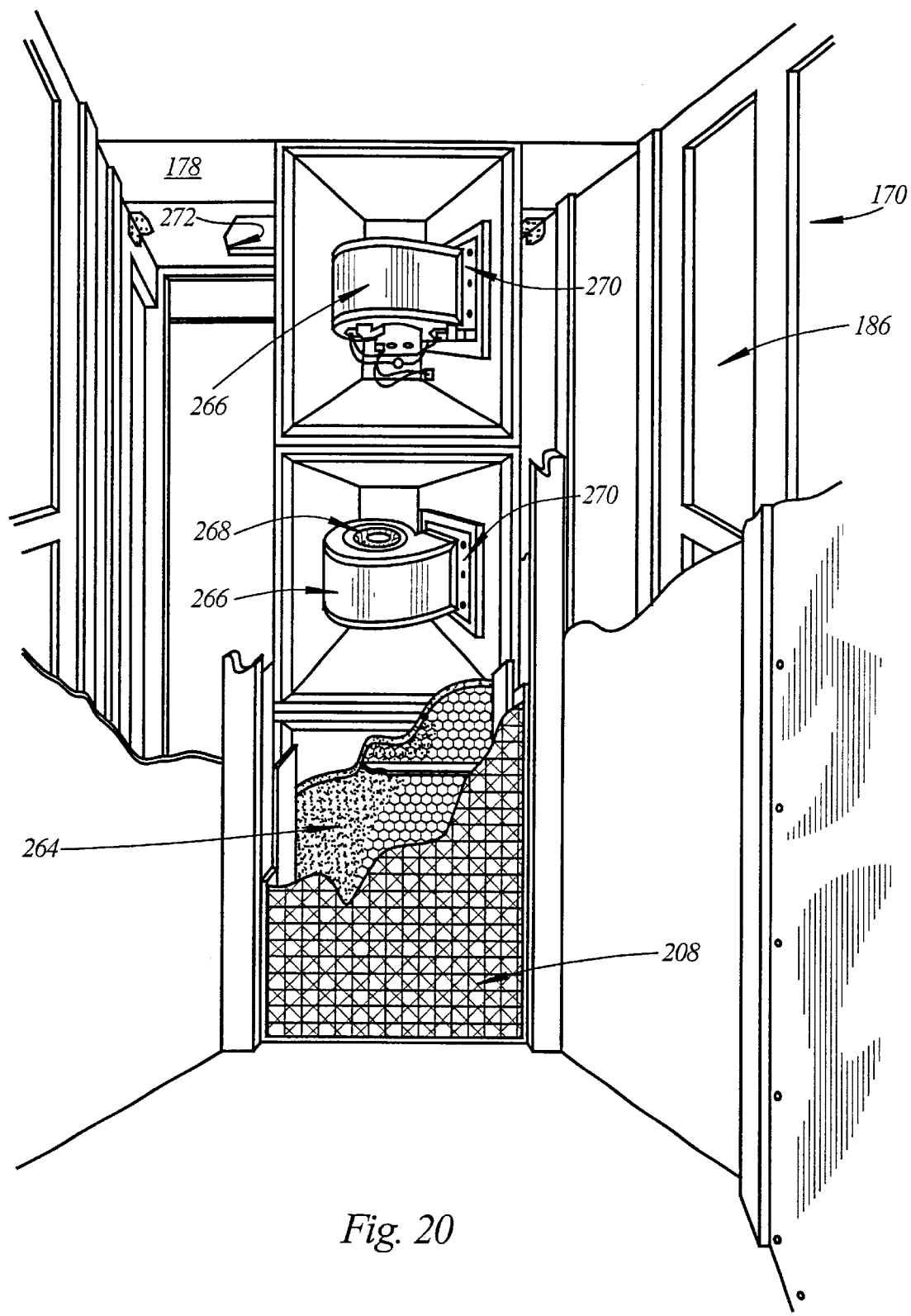
FIG. 20 is an end view further illustrating the apparatus of FIG. 16.

The construction and operation of the mist discharge and confinement zone 186 of the apparatus for automatically coating the human body 170 is further illustrated in FIG. 20. Each of the filter panels 208 overlies a filter 264. The function of the filters 264 is to receive and contain mist discharged from the mist discharge column 196 which is not coated onto the body of a person P situated within the area 190. A suction fan 266 is situated behind each filter 264 and functions to draw mist laden air through its respective filter panel 208 and filter 264. Each fan 266 receives air through an inlet 268 and discharges the air through an outlet 270. Air discharged from the outlets 270 of the fans 266 is directed into the rear of the housing 172. The air then passes through an opening 272 formed in the top assembly 178.

Figure 21:
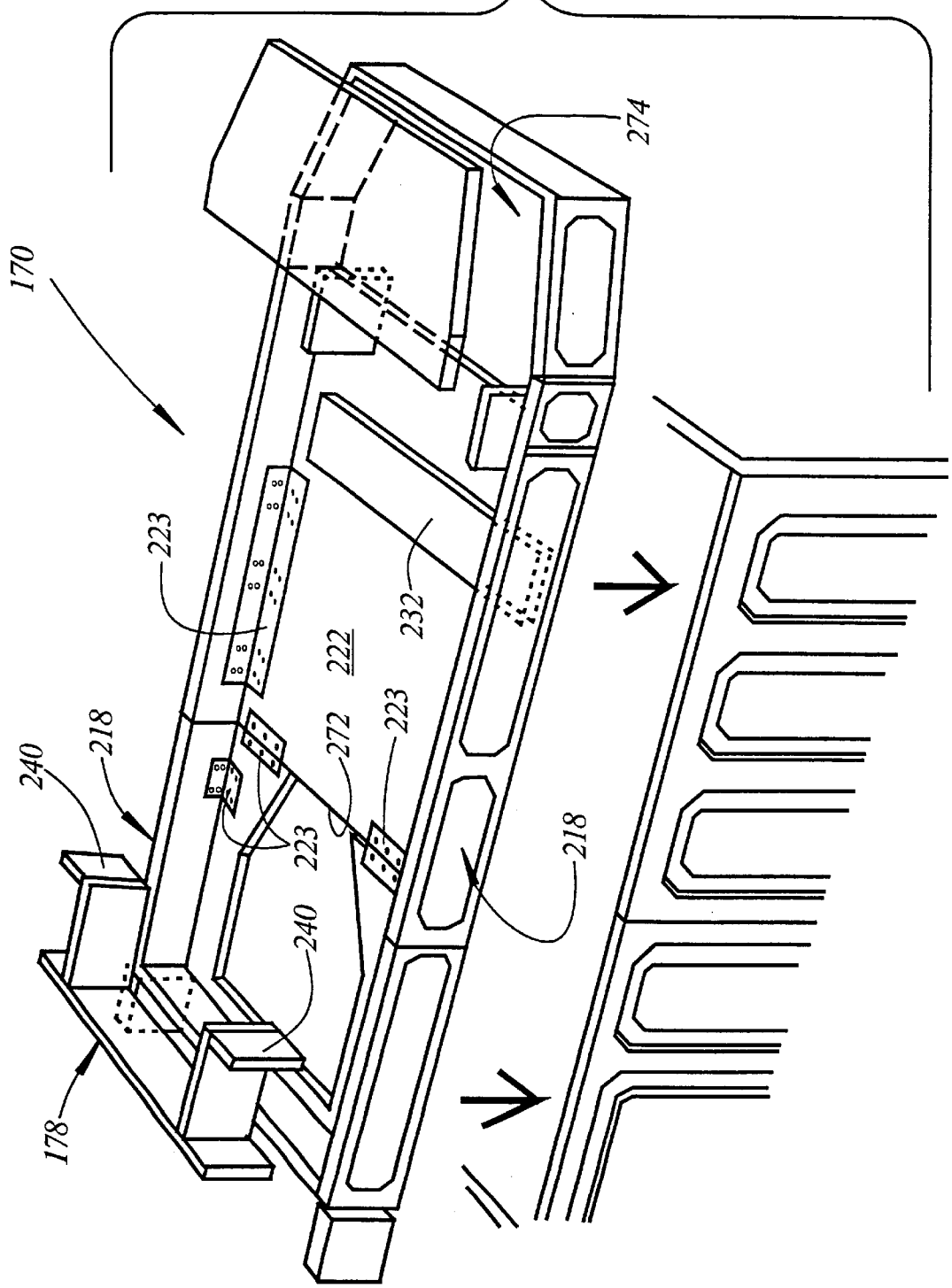
FIG. 21 is an exploded perspective view further illustrating the apparatus of FIG. 16.

Referring to FIG. 21, the construction of the top assembly 178 is shown in greater detail. The opening 272 is situated adjacent the end panel 220 thereof. The top assembly 178 is normally positioned in contact with the ceiling of a room or similar enclosure thereby defining a passageway extending along the horizontally disposed panel 222. The passageway extends to an opening 274 which normally has the mist discharge column 196 extending therethrough. A panel 276 is secured along the upper edges of the side panels 218 of the top assembly 178 and overlies the opening 274. It will therefore be understood that air withdrawn from the mist discharge and confinement zone 186 is returned thereto through the rear portion of the housing 172, the opening 272 formed in the top assembly 178, the passageway extending along the horizontally disposed panel 222 of the top assembly 178, and the opening 274 formed at the opposite end thereof from the opening 272.

Figure 22:
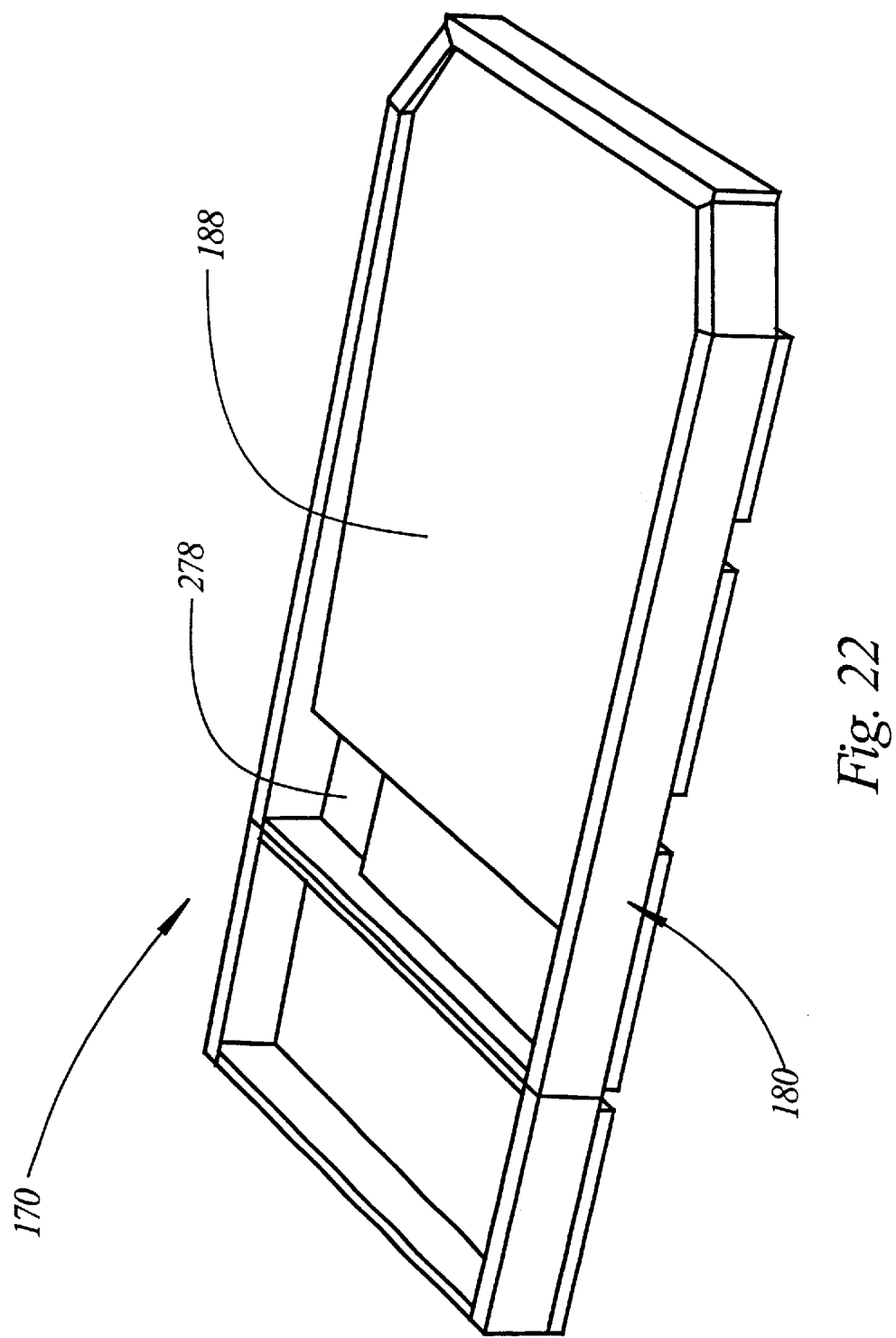
FIG. 22 is a perspective view further illustrating the apparatus of FIG. 16.

The construction of the bottom assembly 180 is shown in greater detail in FIG. 22. The floor 188 slopes downwardly and rearwardly at a shallow angle of about 2 degrees. In this manner, any liquid accumulating on the floor 188 is directed to a sump 278. A conventional sump pump may be utilized to remove liquid from the sump 278 for appropriate disposal.

Figure 23:
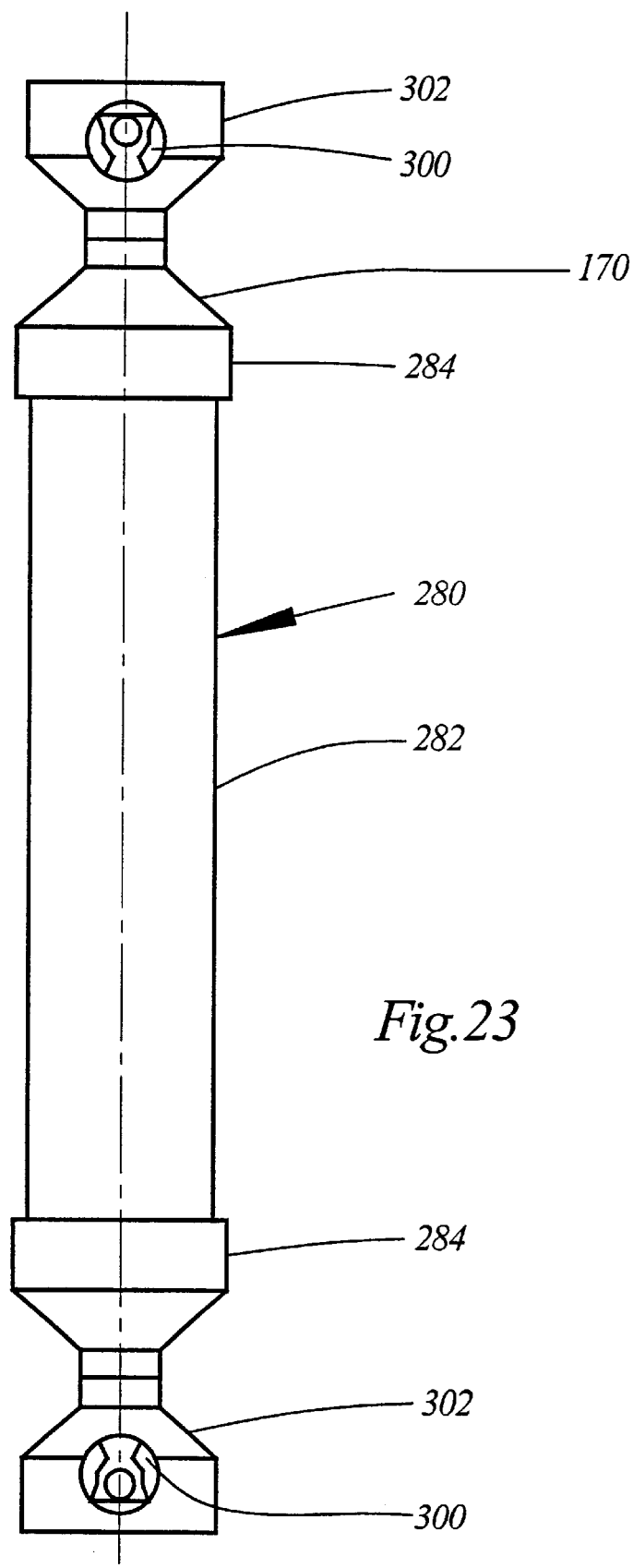
FIG. 23 is an illustration of another component of the apparatus of FIG. 16.
Figure 24:
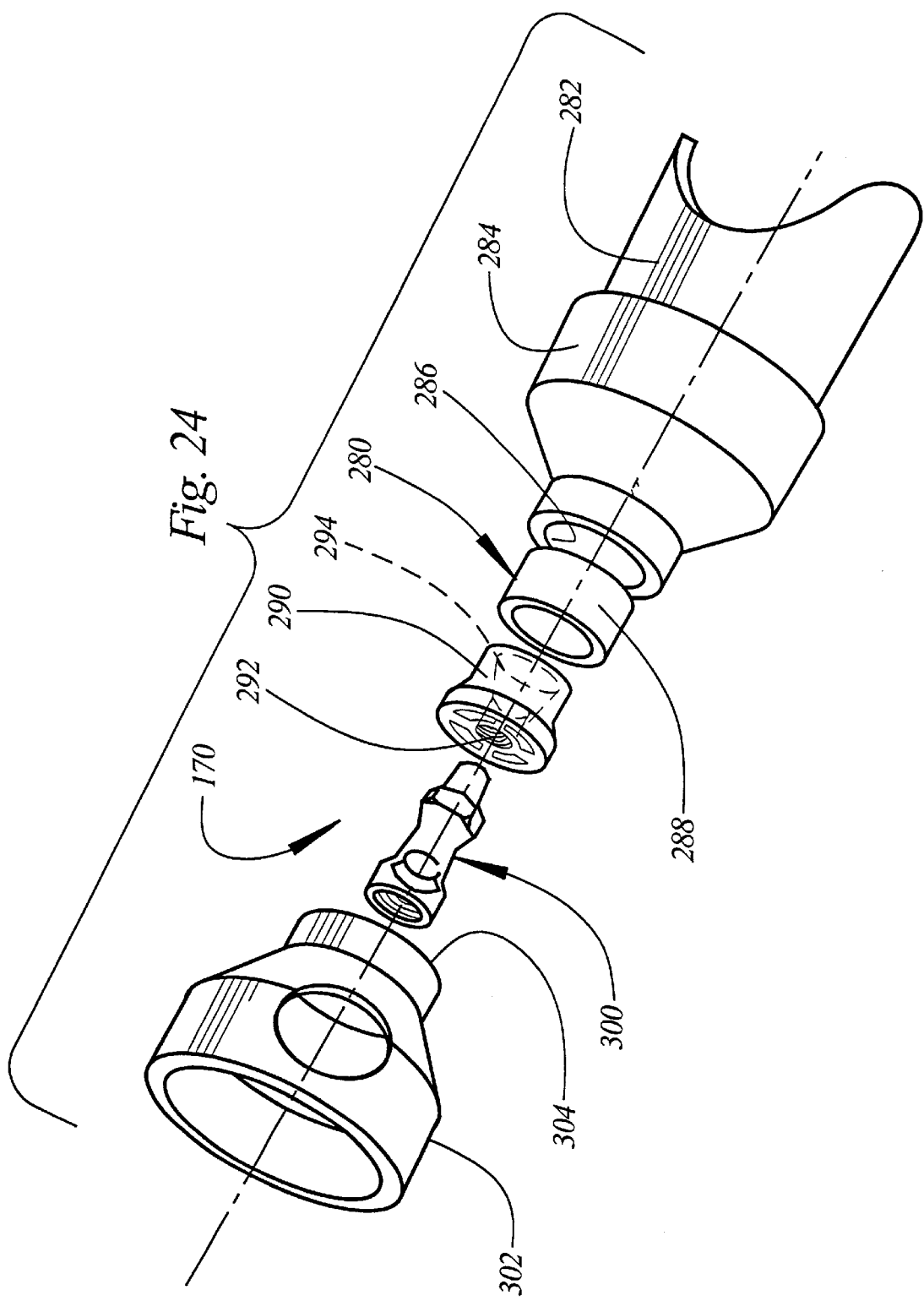
FIG. 24 is a partial exploded perspective view of the apparatus of FIG. 24.

FIGS. 23 and 24 illustrate a self-tanning solution storage and delivery cannister 280 useful in the practice of the invention. As will be apparent by reference to FIG. 23, the opposite ends of the cannister 280 are identical. Therefore, only one end of the cannister 280 is illustrated in FIG. 24.

The cannister 280 includes a central tubular member 282. The central tubular member 282 is preferably transparent in order that the amount of self-tanning solution contained within the canister 280 can be easily determined.

A hollow, conically shaped member 284 is secured to each end of the central tubular member 282. The hollow conical members 284 extend to relatively large apertures 286. A ring shaped member 288 is received in each aperture 286 to reduce the effective diameter thereof.

A plug 290 is received within each ring shaped member 288. Each plug 290 has threaded aperture 292 at one end which flairs to a relatively large diameter aperture 294 at the opposite end. A double quick disconnect valve 300 is threadedly engaged with the aperture 292 of each plug 290. The double quick disconnect valve 300 are preferably identical and are of the type manufactured by the Colder Products. A hollow, conically shaped guard 302 surrounds the double quick disconnect valve 300 and extends to a shoulder 304 which engages the upper end of the hollow, conically shaped member 284. An aperture 306 is provided in each guard 302 to provide access to the double quick disconnect valve 300 protected thereby.

Figure 25:
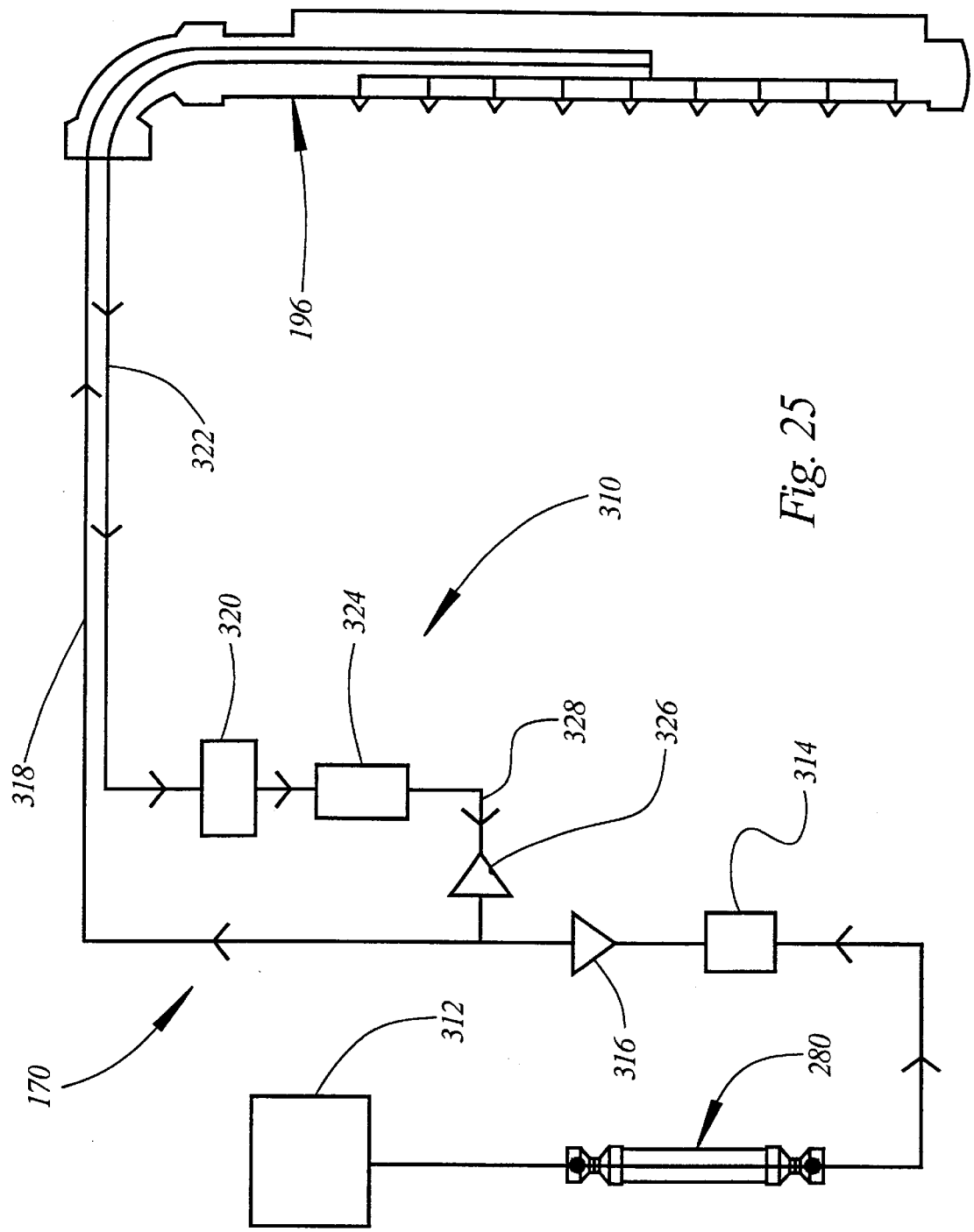
FIG. 25 is a diagrammatic illustration of a recirculation system useful in the practice of the invention.

Referring to FIG. 25, the apparatus 170 is provided with a recirculation system 310. In the operation of prior systems for coating the human body with self-tanning composition, it has been noted that if the coating system stands idle for an extended period of time, the quality of the tans that are achieved during operation of the system immediately following the restarting thereof is different from the quality of tans which are achieved after the system has been operated continuously for an extended period of time. The recirculation system 310 of the present invention overcomes this problem. A canister 280 of the type illustrated in FIGS. 23 and 24 and described hereinabove in conjunction therewith is connected at its upper end to a source of compressed air 312 which typically comprises an air compressor. Compressed air received by the canister 280 from the source 312 is typically at a pressure of about 30 psi.

A self-tanning composition contained with the canister 280 is directed from the bottom thereof through a regulator 314 which reduces the pressure of the self-tanning composition to about 10 psi. From the regulator 314 the self-tanning composition passes through a check valve 316 and a line 318 to the mist discharge column 196.

Self-tanning composition from a canister 280 which is not discharged through the nozzles of the mist discharge column 196 is withdrawn from a column 196 by a pump 320. The pump 320 is connected to the spray column within the mist discharge column 196 through one or more lines 322. Self-tanning composition withdrawn from the mist discharge column 196 by the pump 320 is directed therefrom through a filter 324 and a check valve 326 through a line 328 which is connected in fluid communication with a line 318 at a point between the regulator 314 and the check valve 316.

The pump 320 delivers self-tanning composition to the filters 324 at a pressure which is about 5 psi greater than the pressure within the line 322. As will be apparent, if the nozzles of the mist discharge column 196 are not discharging self-tanning composition, the pressure within the line 318, the mist discharge column 196, and the line 322 remain steady at 10 psi. The pump 320 delivers self-tanning composition to the filter 324 at about 15 psi thereby assuring continuous recirculation of the self-tanning composition through the check valve 326, the line 328, the check valve 316, the line 318, the mist discharge column 196, and the line 322. If self-tanning composition is being discharged from the nozzles of the mist discharge column 196, a pressure drop occurs in the line 318, the mist discharge column 196, and the line 322. Nevertheless, the pump 320 delivers self-tanning composition at a pressure which is approximately 5 psi above the pressure within the line 322, thereby assuring continuing circulation of the self-tanning composition.

In actual practice, the recirculation system 310 of the present invention has been found to provide assurance that the system for automatically coating the human body 170 will deliver uniformly excellent tanning results regardless of whether the system 170 is in continuously or intermittent operation. This is in direct contrast to the performance of prior systems which did not include recirculation wherein the self-tanning results that were achieved after the system had been out of service for whatever reason was found to be substantially different from the results that were achieved when the system was in continuous operation.

Operation

Figure 16:
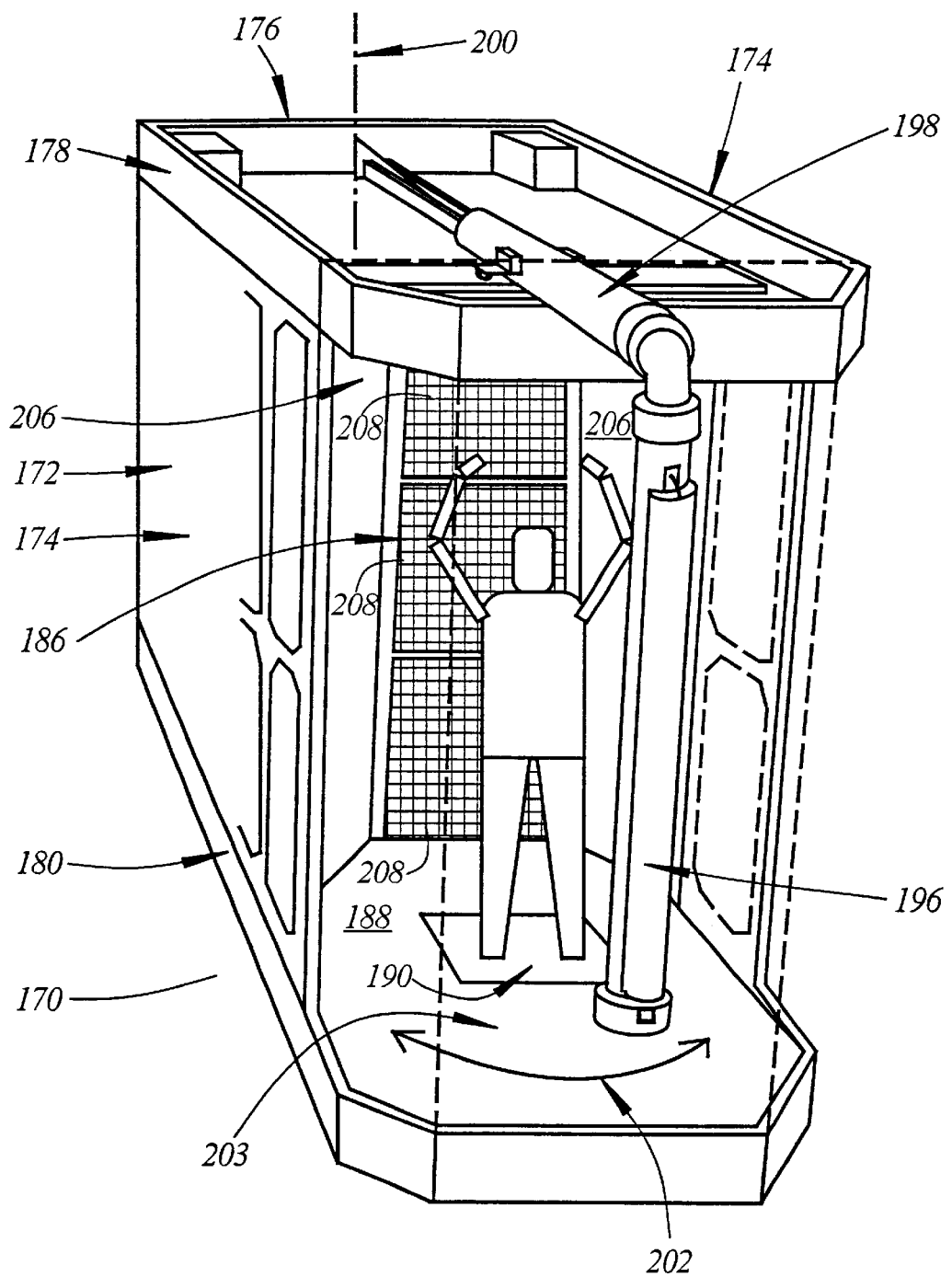
FIG. 16 is a perspective new of a third apparatus useful in the practice of the invention.

Referring particularly to FIG. 16, a person P to be coated enters the mist discharge and confinement zone 186 of the apparatus 170 and stands within the locating area 190. The person P initially faces in the direction of the mist discharge column 196. Upon actuation, the apparatus 170 discharges a predetermined composition, such as a self-tanning composition, from the nozzles of the mist discharge column 196. Actuation of the nozzles to discharge the predetermined composition continues while the mist discharge column is moved from one side of the mist discharge and confinement zone 186 to the other side thereof along the arc 202. During movement of the mist discharge column 196 along the arc 202, the predetermined composition may be discharged from one or more zones each including one or more nozzles either simultaneously, sequentially, or independently. The preferred operation is 7 seconds of forward motion of the column through the arc. There is continuous misting for about 6 seconds of such motion. The column returns to its original position in the next 8 seconds.

When the mist discharge column 196 reaches the opposite end of the arc 202 from its point of origin, the person P turns 90° so as to position one side in the direction of the mist discharge column 196. The mist discharge column 196 then moves back along the arc 202 to its point of origin. The predetermined composition is discharged from the mist discharge column simultaneously with the movement thereof along the arc 202.

When the mist discharge column 196 reaches its original positioning, the person P turns another 90° so as to be facing directly away from the mist discharge column 196. The mist discharge column 196 is then moved along the arc 202 from one side of the mist discharge and confinement zone 186 to the other. During movement of the mist discharge column 196 along the arc 202, the predetermined composition is discharged from the nozzles comprising the mist discharge column 196. As is the case in each path of the mist discharge column 196, the zones comprising multiple nozzles mounted on the mist discharge column 196 may be operated simultaneously, sequentially, or independently.

After the mist discharge column 196 has moved to the opposite side of the mist discharge and confinement zone 186 from its point of origin, the person P turns another 90° so as to position the last of four sides facing the mist discharge column 196. The mist discharge column 196 then moves back along the arc 202 to its point of origin. Once again, discharge of the predetermined composition from a nozzle comprising the mist discharge column 196 occurs simultaneously with the movement thereof back to its point of origin. The entire operating cycle comprising all four positionings of the person P in the area 190 requires about 60 seconds.

Throughout the operation of the apparatus 170 comprising movement of the mist discharge column 196 back and forth along the arc 202, the suction fans 266 are operated to withdraw excess mist from the mist discharge and confinement zone 186 for containment in the filters 264. Any fluid which engages the floor 188 flows along the sloping surface thereof and is received in the sump 278 for proper disposal. In this manner, the discharge from the nozzles comprised in the mist discharge column 196 is completely contained.

FIGS. 26–36, inclusive, illustrate an embodiment of the invention employing stationary mist discharge nozzles as opposed to the nozzles engineered for movement relative to a person to be coated. The basic principle behind the virtual motion concept is demonstrated in FIGS. 26–36.

Figure 26:
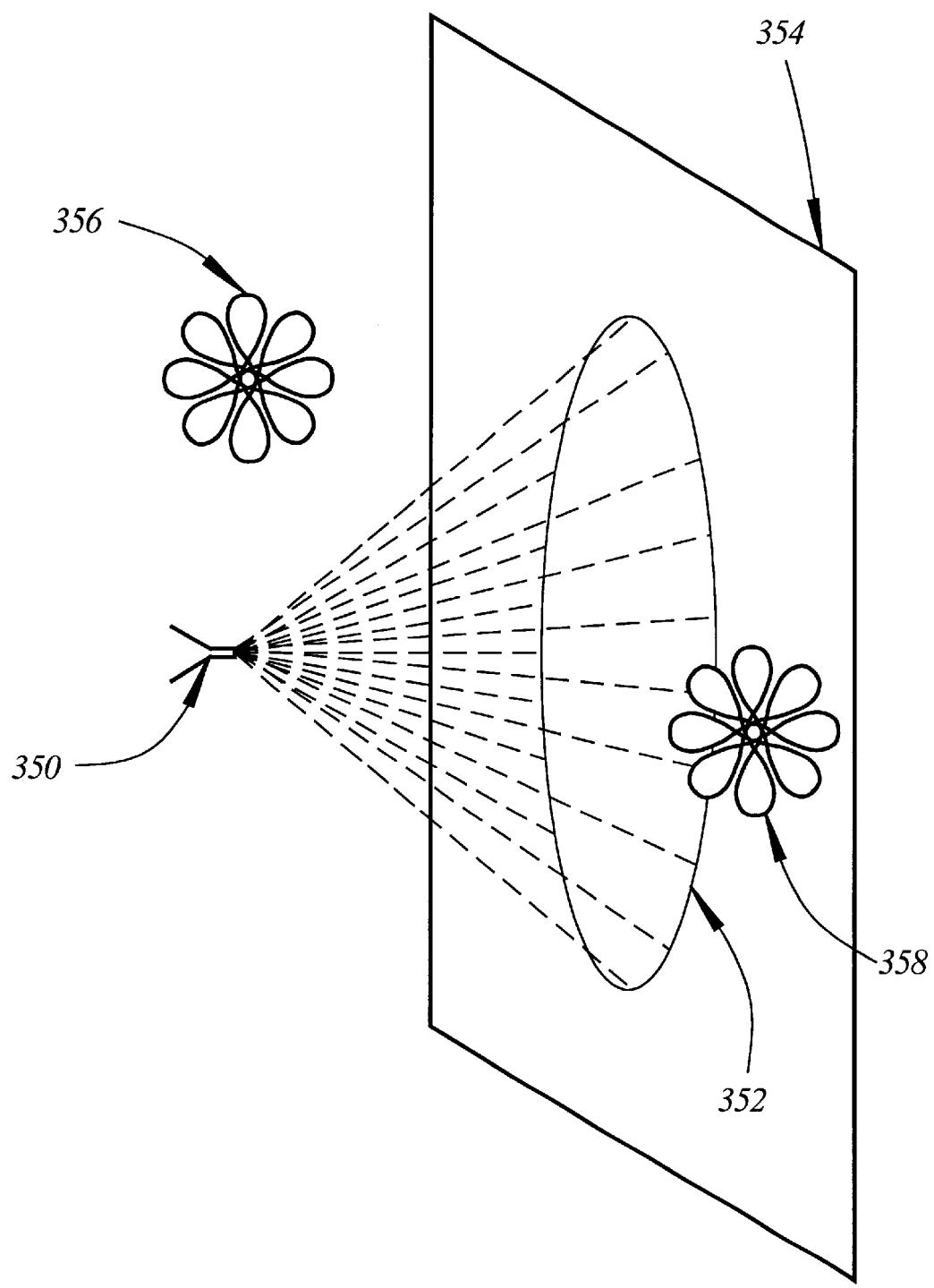
FIG. 26 is a diagrammatic illustration of a fourth apparatus useful in the practice of the invention.
Figure 27:
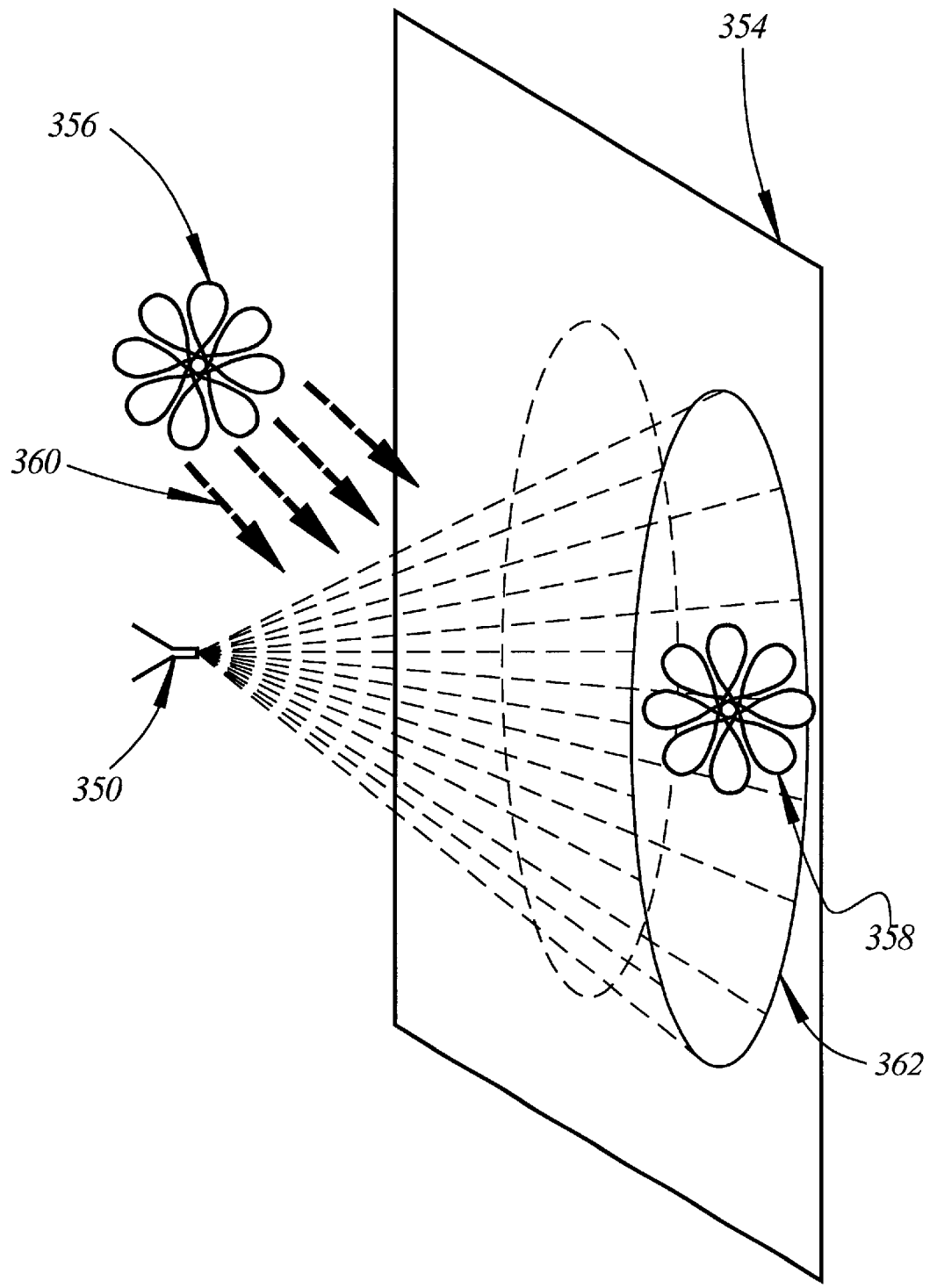
FIG. 27 is a diagrammatic illustration of the apparatus of FIG. 26 at a different stage of its operation.
Figure 28:
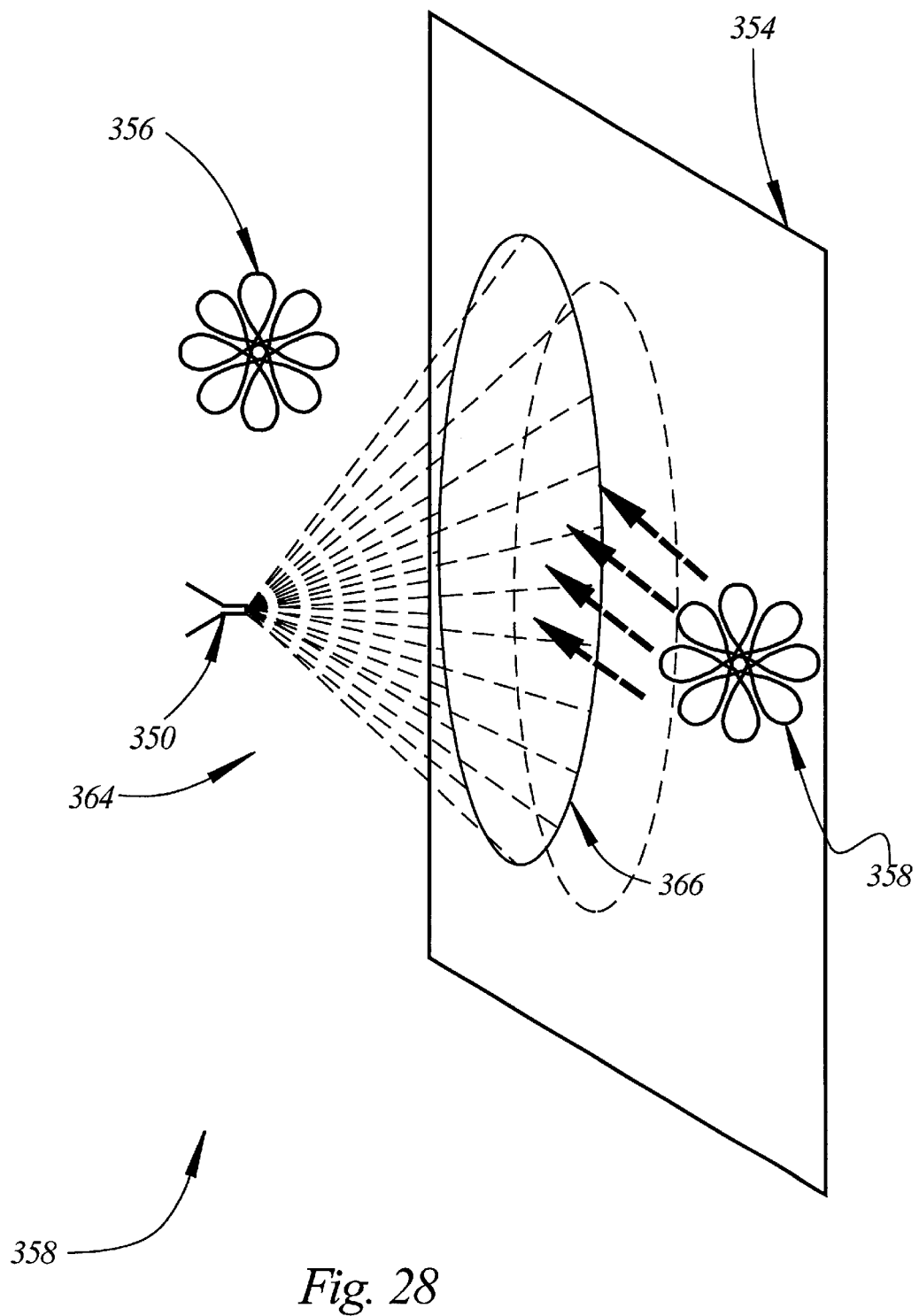
FIG. 28 is a diagrammatic illustration of the apparatus of FIG. 26 at a still different stage of its operation.

Referring first to FIGS. 26, 27, and 28 a stationary mist discharge nozzle 350 normally discharges mist into a targeted coverage area 352 within a zone 354. At this point air jets 356 and 358 located on opposite sides of the stationary nozzle 350 and diagrammatically illustrated by fan configurations, are both in the "off" condition.

In FIG. 27 the air jet 356 is illustrated in the "on" condition thereby causing air to sweep across the path of the mist discharged from the stationary nozzle 350 as indicated by the arrows 360. Operation of the air jet 356 causes the spray pattern generated by operation of a stationary nozzle 350 to move relative to the zone 354 from the coverage area 352 illustrated in FIG. 26 to the location 362 illustrated in FIG. 27. The extent of displacement of the zone by air jets 356 and 358 can be controlled by varying the direction, intensity, and volume of the air jets.

The opposite movement of the coverage area 352 is illustrated in FIG. 28. Airjet 356 is now in the "off" condition while air jet 358 is in the "on" condition. Air from the air jet 358 flows across the path of the mist generated by the stationary nozzle 350 as indicated by the arrows 364. This causes the spray pattern generated by operation of the stationary nozzle 350 to move from the location 362 illustrated in FIG. 27 through the location 352 of FIG. 26 to a coverage area 366 relative to the zone 354. Thus, by selective operation of the air jets 356 and 358, including variations in the intensity of operation thereof, the positioning of the spray pattern generated by the stationary nozzle 350 can be selectively positioned relative to the zone 354. As will be appreciated by those skilled in the art, additional air jets can be positioned relative to the periphery of the spray pattern generated by the stationary nozzle 350 thereby facilitating location of the spray pattern generated by the stationary nozzle 350 at any desired location relative to the zone 354.

Figure 29:
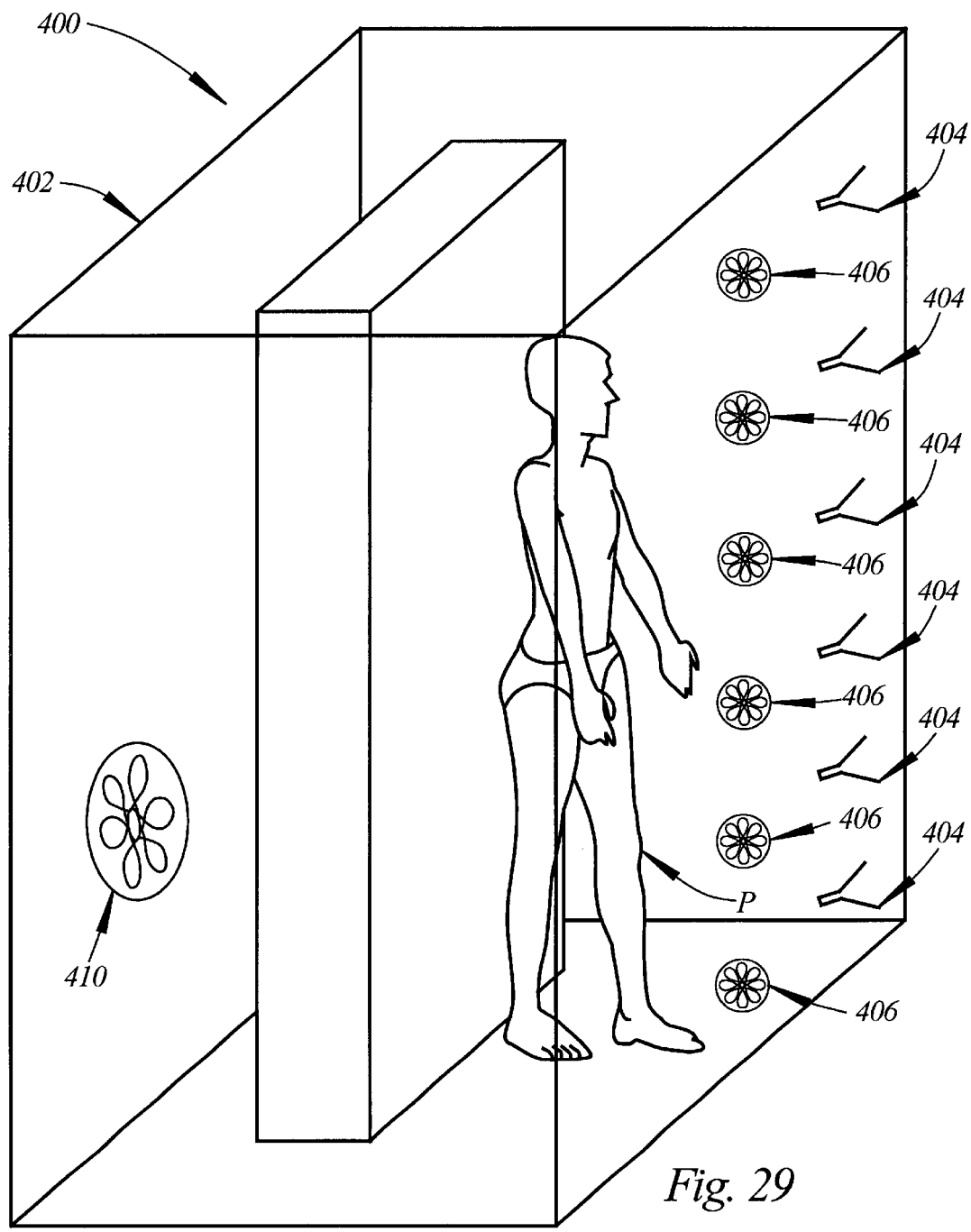
FIG. 29 is a perspective view of an apparatus for coating the human body comprising the apparatus of FIGS. 26, 27, and 28.

A system 400 for automatically coating the human body is illustrated in FIG. 29. The system 400 employs a plurality of stationary mist generating nozzles and air jets for selectively positioning the spray patterns generated by the stationary mist generating nozzles in the manner illustrated in FIGS. 26, 27, and 28 and described hereinabove in connection therewith.

A coating chamber 402 receives therein the entire body of the person P to be coated. A plurality of stationary mist generating nozzles 404 are positioned within the coating chamber 402 in a single vertical column relative to the person P situated therein. Each stationary mist generating nozzle 404 has an air jet 406 associated therewith. During operation of the system 400, the airjet 406 associated with each nozzle 404 is selectively operated to position the spray pattern generated by the associated nozzle 404 relative to the person P within the coating chamber 402. In this manner the body of the person P within the chamber 402 is uniformly coated without moving the nozzles 404.

The coating system 400 may further include a discharge fan 410 for removing excess coating material from the coating chamber 402 and for directing the excess coating material to a filter (not shown in FIG. 29). In the preferred mode of operation, the discharge fan 410 is "off" during the brief period that misting is occurring.

The coating process of FIG. 29 is diagrammatically illustrated in FIGS. 30–36, inclusive. A stationary mist generating nozzle 420 has an air jet 422 associated therewith, the air jet 422 being diagrammatically illustrated by a fan configuration. A person P to be coated with mist generated by the stationary nozzle 420 as situated within a coating chamber 424.

Figure 30:
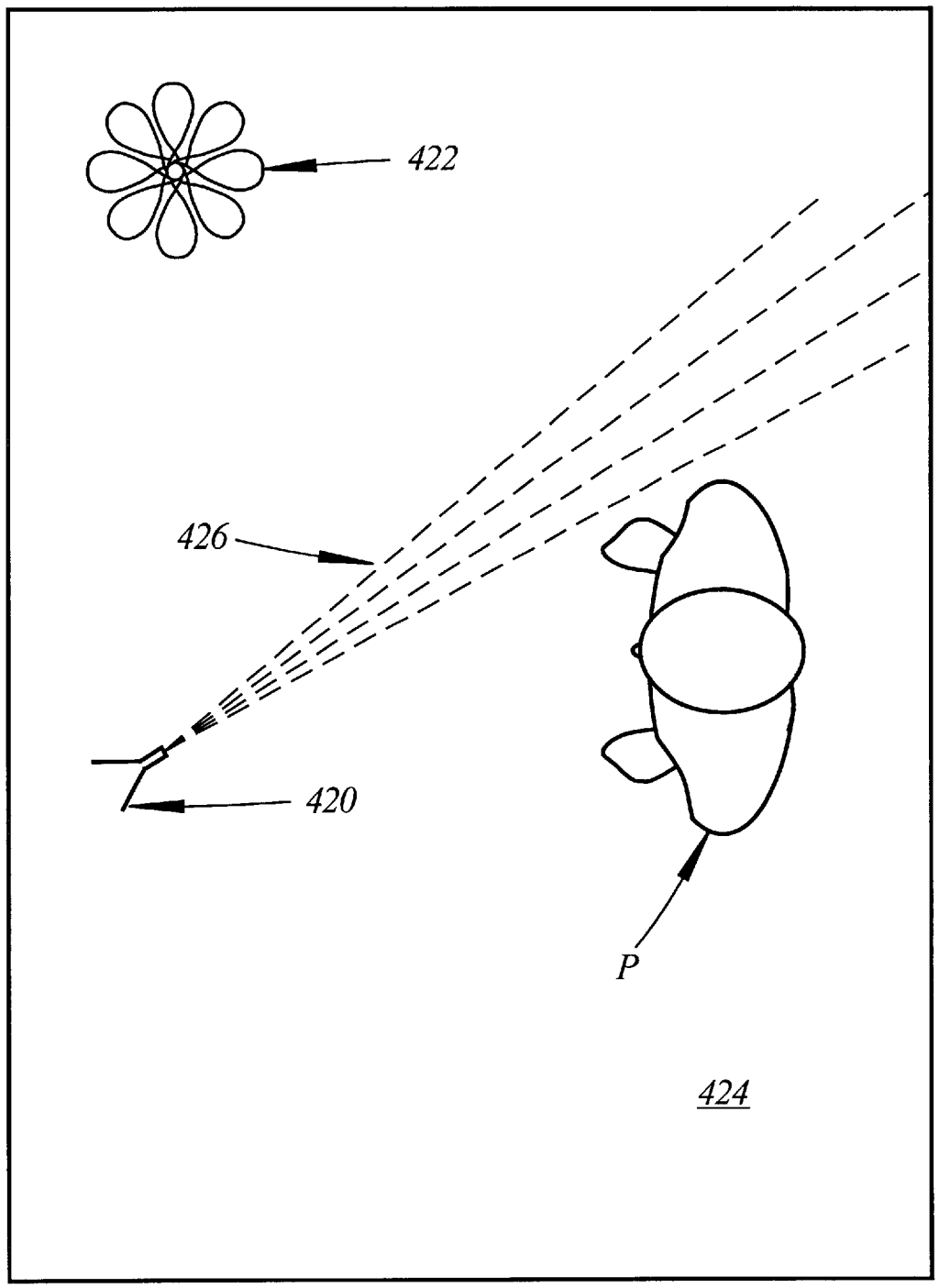
FIG. 30 is a diagrammatic illustration of a first step in the operation of the apparatus of FIG. 29.
Figure 31:
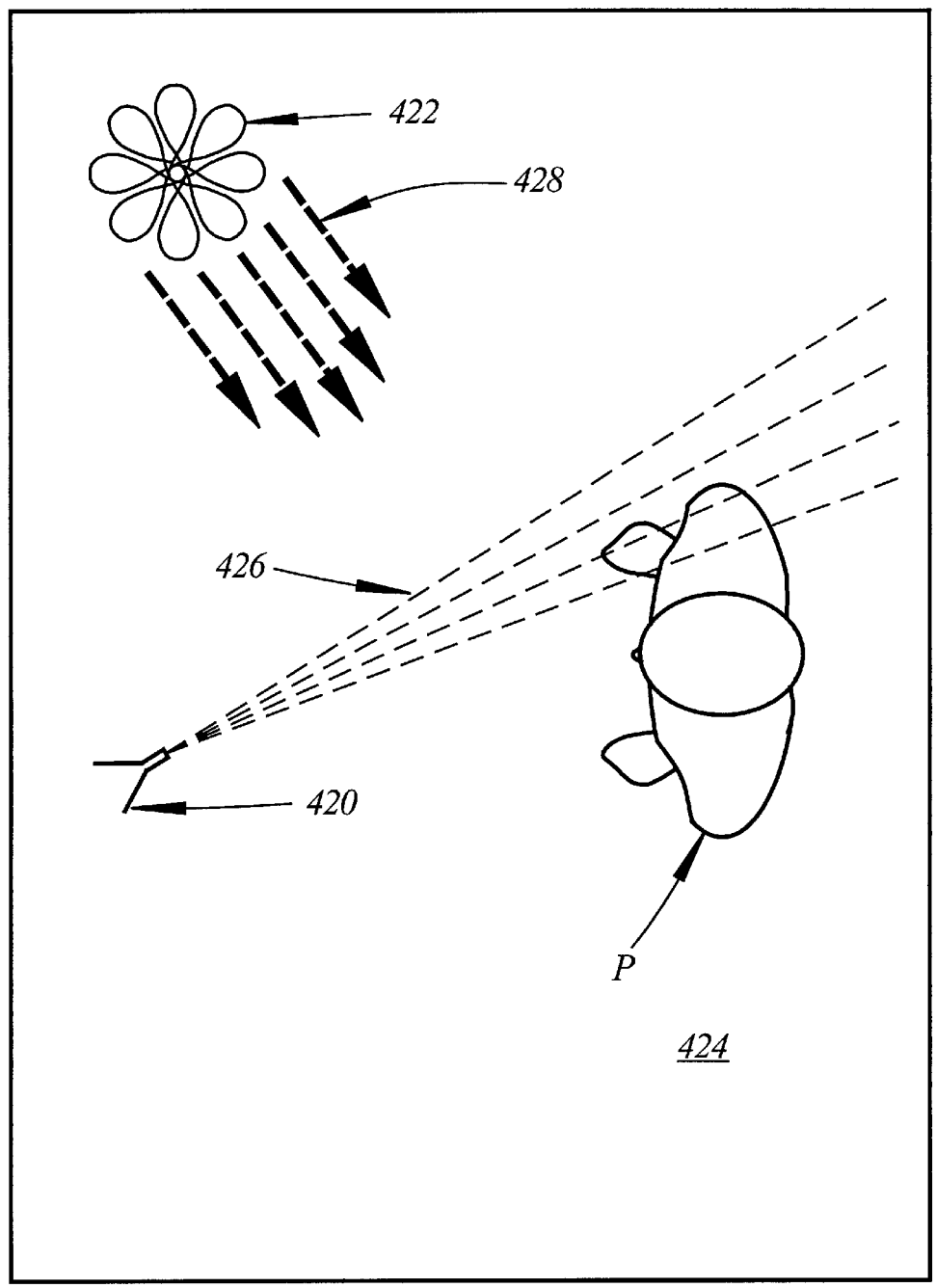
FIG. 31 is a diagrammatic illustration of a somewhat later step in the operation of the apparatus of FIG. 29.
Figure 32:
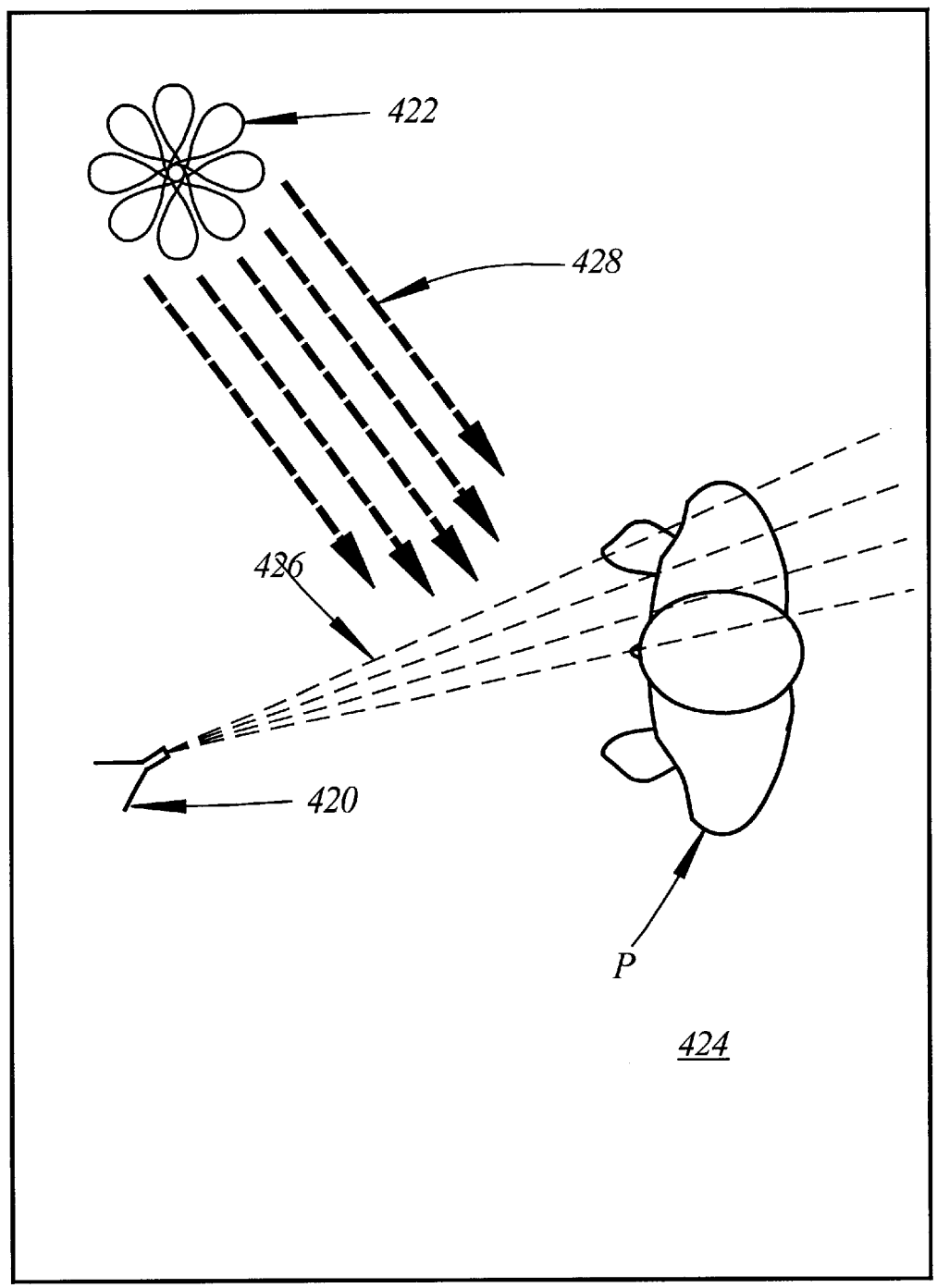
FIG. 32 is a diagrammatic illustration of a later step in the operation of the apparatus of FIG. 29.
Figure 33:
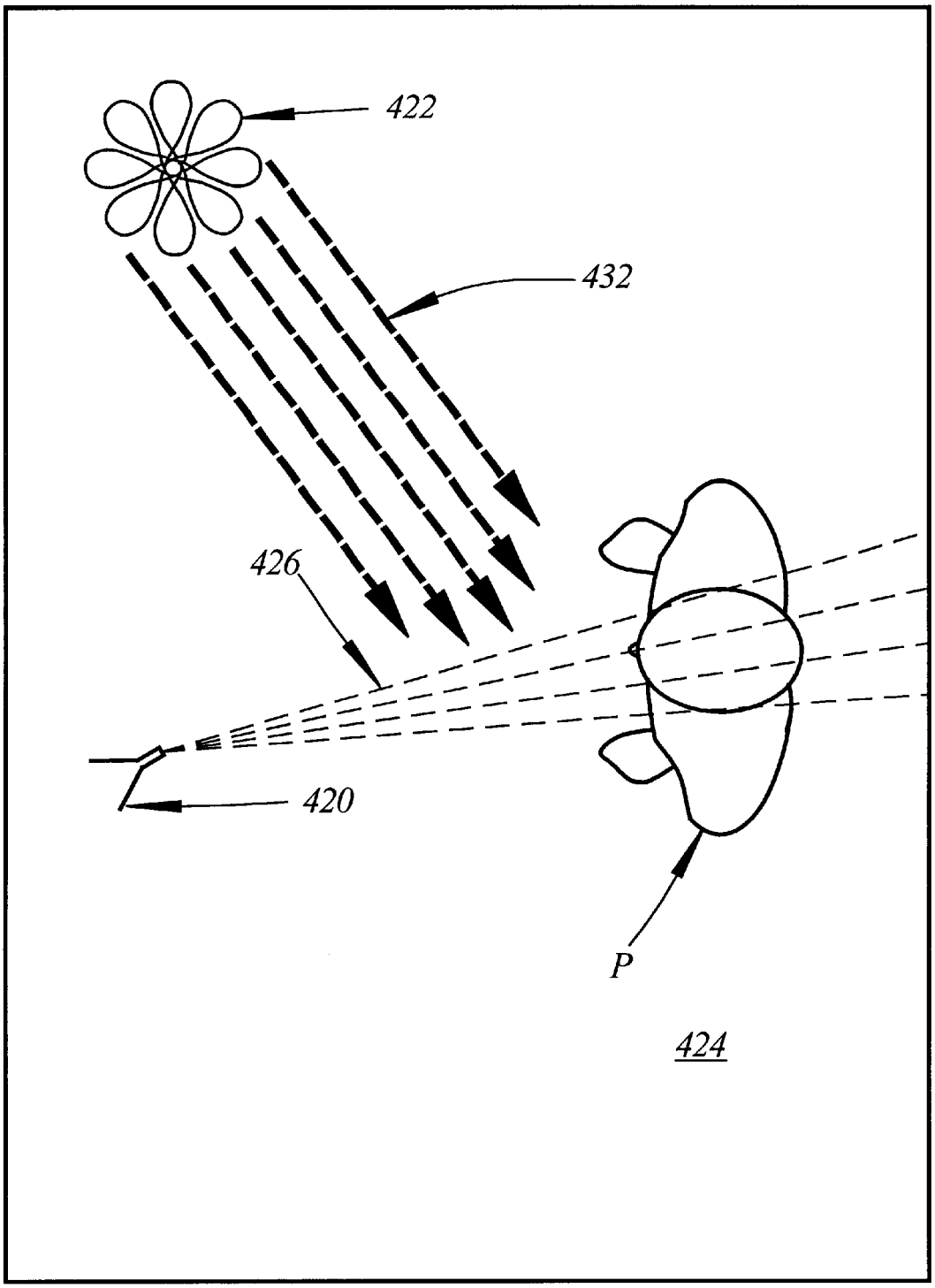
FIG. 33 is a diagrammatic illustration of a still later step in the operation of the apparatus of FIG. 29.
Figure 34:
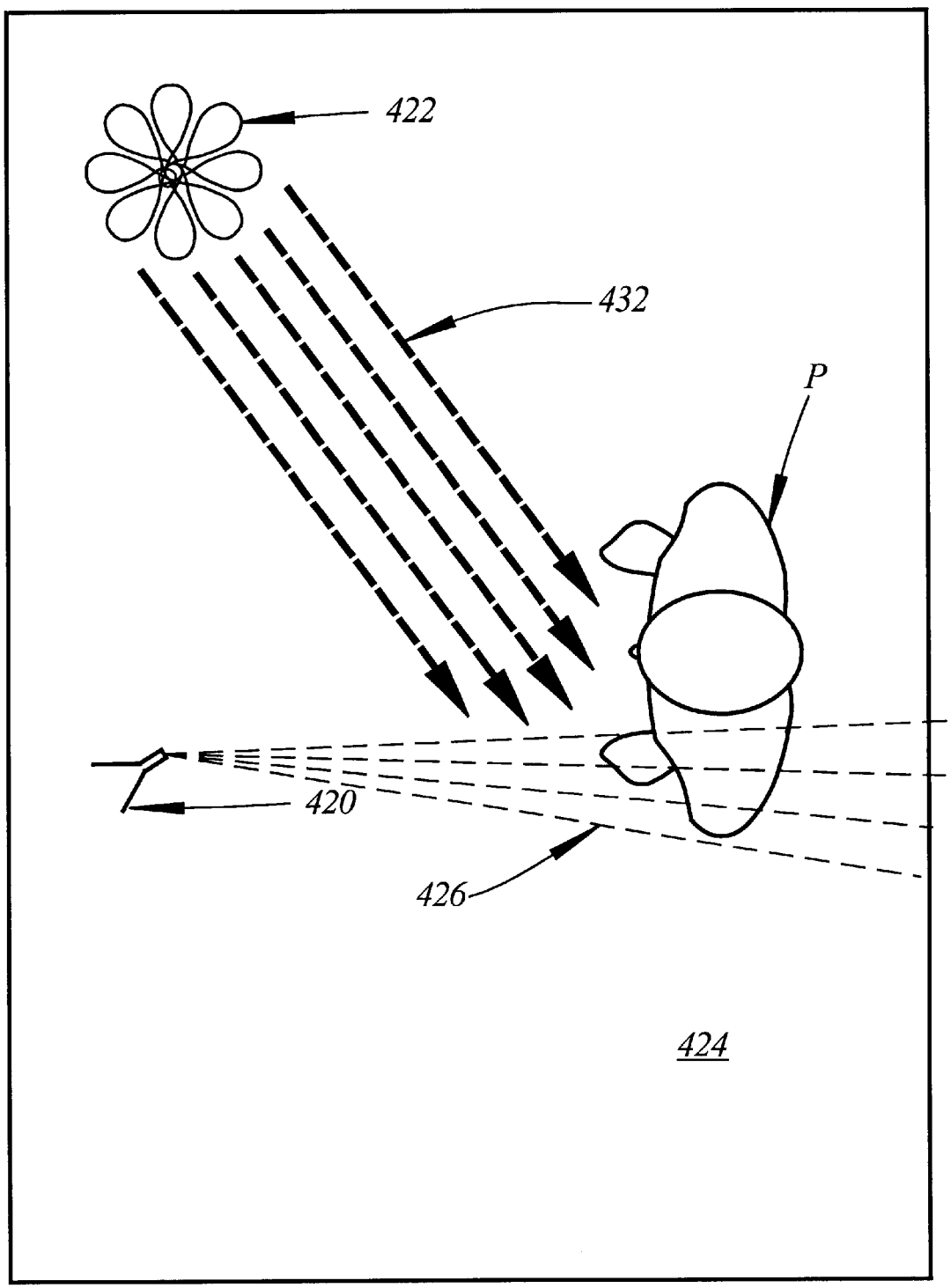
FIG. 34 is a diagrammatic illustration of yet another step in the operation of the apparatus of FIG. 29.
Figure 35:
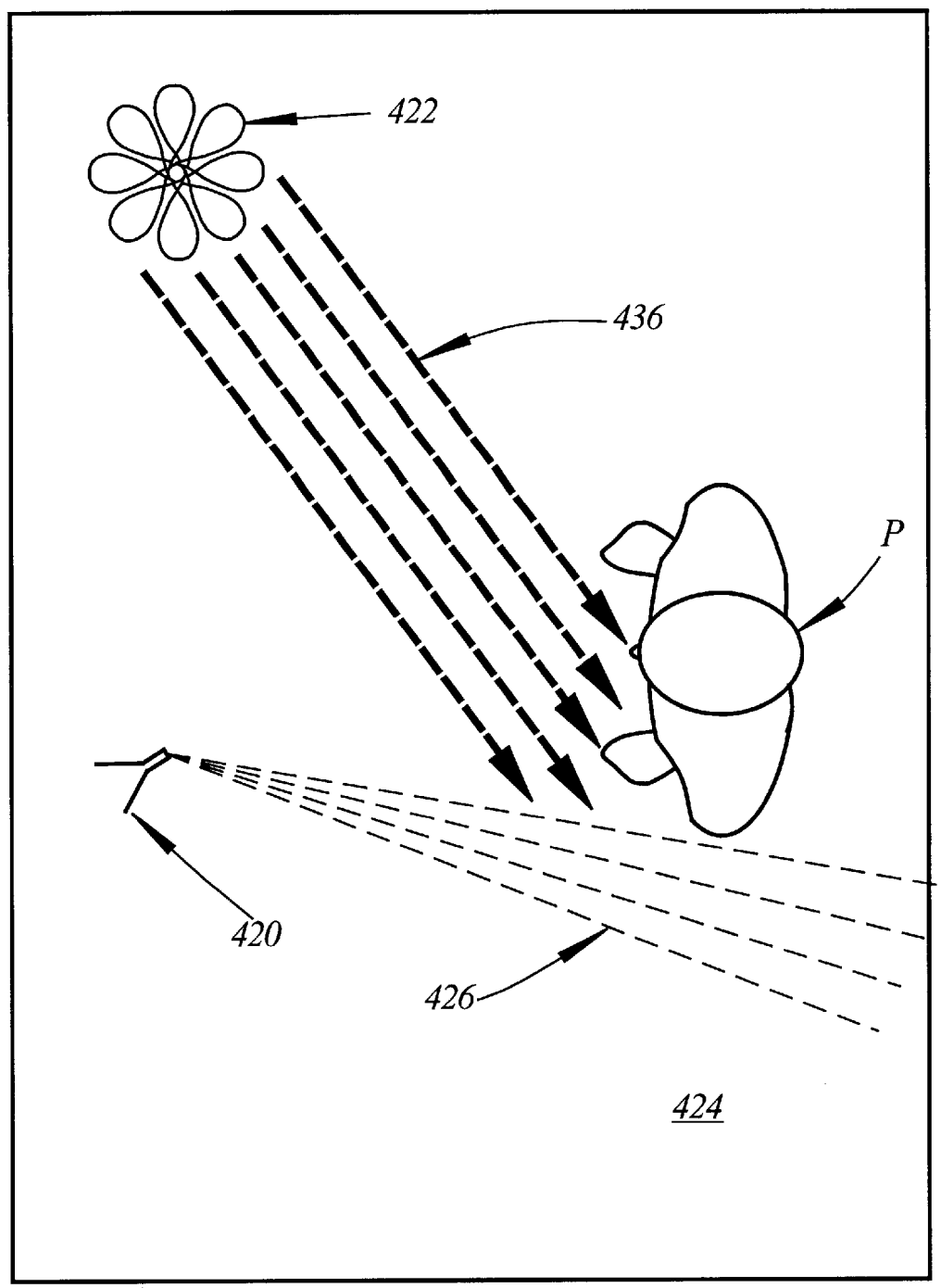
FIG. 35 is a diagrammatic illustration of a final step in the operation of the apparatus of FIG. 29.

In FIG. 30 the airjet 422 is in the "off" condition. As this point the spray pattern 426 generated by the stationary nozzle 420 passes in front of the person P. In FIG. 31 the air jet 422 is in the "on" condition but is operated to generate a relatively low air flow rate as indicated by the arrows 428, thereby causing the spray pattern 426 generated by the stationary nozzle 420 to partially engage the person P within the coating chamber 424. In FIG. 33 the air flow rate from the air jet 422 is substantially increased as indicated by the arrows 430 thereby substantially increasing the engagement of the spray pattern 426 from the stationary nozzle 420 with the person P. In FIG. 34 the air flow rate from the air jet 422 is still further increased as indicated by the arrows 432 thereby causing the spray pattern 426 from the stationary nozzle 420 to further engage the person P. In FIG. 35 the airjet 422 is operated at maximum power as indicated by the arrows 436 thereby causing the spray pattern 426 from stationary nozzle 420 to move beyond the person P within the coating chamber 424.

It will therefore be understood that in accordance with the embodiment of the invention illustrated in FIGS. 26–35, inclusive, and described hereinabove in connection therewith, a human body coating composition is discharged from one or more stationary mist generating nozzles. The discharge pattern generated by the mist discharge nozzle(s) is located relative to a person to be coated by one or more air jets each associated with a particular stationary mist generating nozzle. When a plurality of air jets are associated with each mist generating nozzle, the discharge therefrom can be selectively moved horizontally and vertically thereby uniformly coating the entire human body without requiring either movement of the mist generating nozzles or movement of the person being coated with respect thereto.

Figure 36:
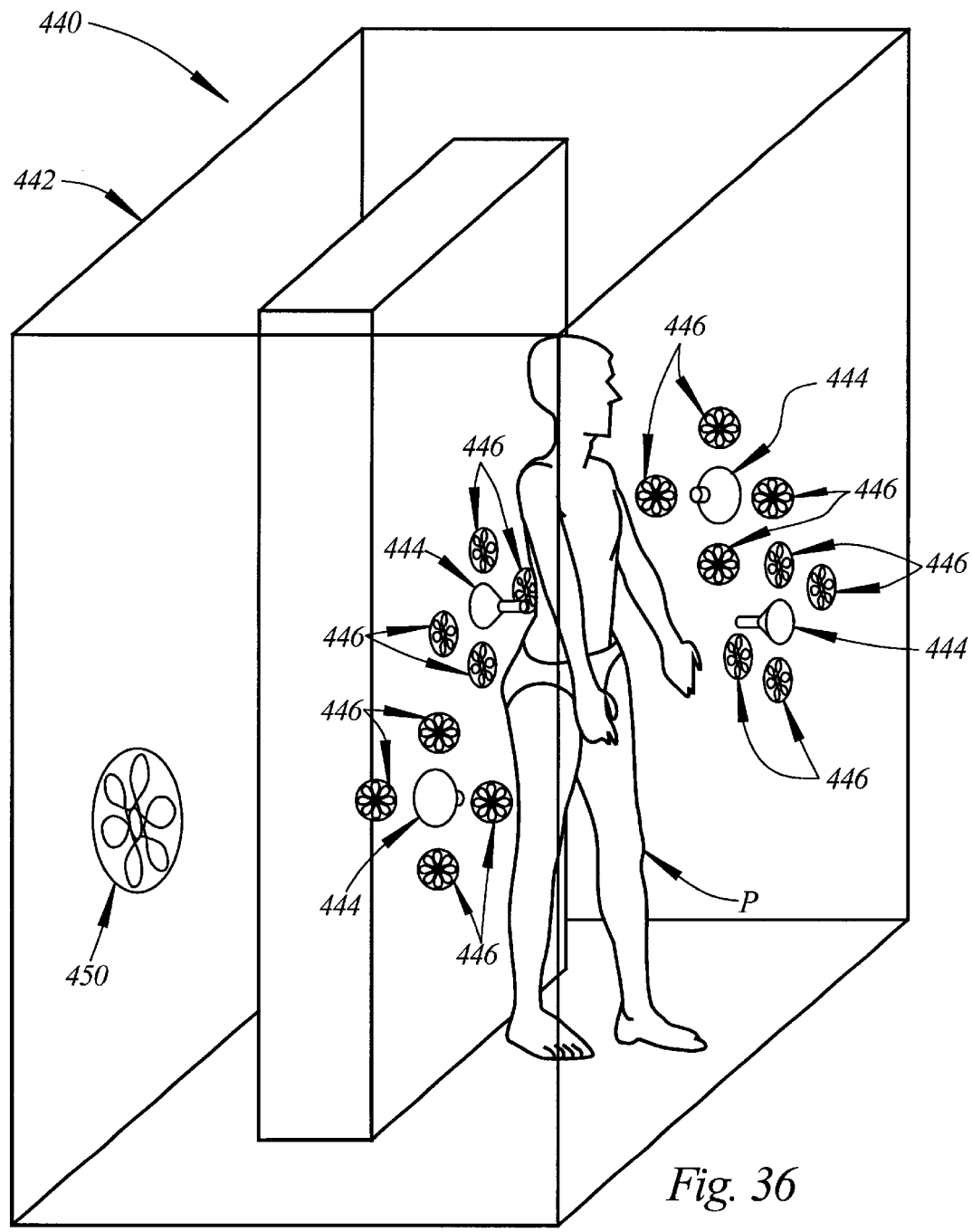
FIG. 36 is a diagrammatic illustration of a system for automatically coating the human body in which stationary nozzles and air jets are positioned at spaced intervals around the entire body of the person being coated.

FIG. 36 illustrates a system for coating the human body 440 including a coating chamber 442 which receives a person P therein. A plurality of stationary mist generating nozzles 444 each have plurality of air jets 446 associated therewith. The nozzles 444 and the air jets 446 are located at spaced intervals around the entire body of the person P to be coated. By means of the embodiment of FIG. 36, the entire body of the person can be coated simultaneously, it being understood that the air jets 406 function to selectively position the spray from their associated nozzles 404 both horizontally and vertically relative to the person P.

An exhaust fan 450 may be employed to remove excess spray. Preferably the fan 410 is not operated during the brief misting sequence.

Features Contributing Significantly to the Successful Operation of an Automated Coating System for the Human Body Incorporating the Invention Formula:

The following formula is a combination of water, dihydroxyacetone, bronzer, moisturizer, surfactant, and penetration enhancer. The formula is:

|  |  | Range | Preferred |
| --- | --- | --- | --- |
| water | base | 16%–65% | 41.7% |
| dihydroxyacetone | self-tanning | 3%–15% | 10.0% |
| bronzer* | cosmetic colorant | 0%–10% | 8.0% |
| ethoxy diglycol | penetration enhancer | 0%–10% | 5.0% |
| commercial moisturizer lotion** | film former, viscosity | 10%–25% | 15.0% |
| commercial bath product*** | surfactant | 0%–2% | 0.6% |
| citric acid | pH adjustment | 0.1%–1.0% | 0.2% |
| 10x aloe vera concentrate | moisturizer, tan enhancer | 1%–5% | 2.5% |
| isopropyl alcohol with methyl salicylate | solvent, penetration enhancer | 5%–25% | 15% |
| Trivosol ® | emulsifier | .5%–10% | 2% |

*By way of example, a suitable bronzer would be a combination of the following food dyes provided by Adams Extract Company, Austin, Texas: 4 parts red, 2 parts yellow, 1 part green, and 3 parts purple.
**By way of example, a suitable commercial moisturizer lotion includes Vaseline Intensive Care Lotion (Aloe Vera Triple Action Formula, Chesebrough-Ponds, Greenwich, CT).
***By way of example, a suitable commercial bath product includes Vaseline Intensive Care Foaming Crème Bath (Chesebrough-Ponds, Greenwich, CT).

Foot Shields:

The feet are one of the most difficult parts of the body to coat uniformly. This difficulty is due in large part to the irregular structure of feet. Also, the downward motion of the atomized mist, both by gravity and from air currents, tends to cause the mist to settle on the tops of the feet. Therefore, the feet are provided with shields to assure a more uniform coating of the feet. The shields may take the form of a large, bottomless shoe. The shields produce a silhouette effect from the top of the feet to the toes. Holes and openings are provided in the shields which are located 0.25 to 2 inches from the feet, allowing the mist to result in a silhouette effect rather than defined lines.

Air Shield to Deflect Air Away From the Feet:

To reduce the amount of mist settling on the feet, a plastic shield shaped like a figure eight is placed between the fleximat flooring the user stands on and the metal grating supporting the fleximat. Dimensions of the figure eight are two 18 inch diameter overlapping circles with a total width of 26 inches. The total width can vary from 18 inches to 36 inches, and the circle diameters can vary from 12 inches to 20 inches.

Toweling Buffing After Coating:

After coating it is advantageous to use a towel rub to buff over the entire body to yield a more uniform coating and to remove any areas of excess. The toweling yields a more cosmetically pleasing result and reduces transfer to clothing. It is preferred to towel using long, light strokes. A cotton bath towel 16 inches by 32 inches may be used. The towel could vary from a hand cloth (8"×8") to a large beach towel (18"×48"). Care must be taken not to rub so hard or too much as to rub off the coating (or tan). Basically, the weight of the preferred towel is adequate, without additional pressure.

Stance During Coating:

The stance used during the coating is important. After trial and evaluation of numerous methods, it has been discovered that the "ballerina stance" seems to work best. Key elements of the stance are:

hands over the head
  preferred 2 inches
  lower limit—hands touching head
  upper limit—arms extended fully up
hands parallel to the floor
  hands could be, but not recommended to be, perpendicular to floor in a praying stance, or facing downwardly
feet separated about 12 inches
  to allow mist to coat inside of legs
  feet are flat on flooring
  use of feet shields as described above
Hair Net:

Although the above-described self-tanning solution does not turn hair orange, it may accumulate on hair. To avoid this accumulation, the user can wear a hair net or bouffant. Preferred compositions for the hair net include a cloth or plastic mesh or a continuous plastic sheet.

Barrier Cream:

It has been discovered that the commercial barrier cream produced by GoJo blocks the tanning solution from the skin. During the coating process, this lotion can be used to prevent tanning of specific areas, such as the palms of the hands.

High Efficiency Filter:

The use of high efficiency filters to remove excess mist is important. Preferably, a Binks high-efficiency paint-pockets filter is used.

Recharging of Filter:

It has been discovered that the tanning solution trapped in the filter can be removed with a water rinse. The solution, which is water soluble, is flushed out using water that is back-washed (water applied to the top surface opposite of the surface facing the solution) or water, preferably under moderate (greater than 60 psi) pressure, that is hosed on the filtered surface.

Uniform Air Flow:

Uniformity of air flow is very important to assure that the mist continues to be applied uniformly over the body even after the pressurized spray stops. Air flow parameters are, in the downward motion:

| | |
|---|---|
| most preferred | 100 cfm |
| next preferred | 50 cfm to 200 cfm |
| next preferred | 25 cfm to 300 cfm |

Warming of Air:

Atomization of liquids as done here by the nozzles results in a significant reduction in liquid temperature (as much as 20° F.). To keep the temperature to a warm, pleasant experience, four halogen lamps (250 watts each) can be added to the system to provide both illumination and heat. A coating chamber temperature of 80° F. to 110° F. is preferred, with 90° F. to 100° F. being more preferred. Other heating devices include infrared lamps and electrical heating elements.

EXAMPLES

Example 1

A twenty year old female of type III skin tanned by this process. She first applied a heart shaped sticker on her right arm. She covered her hair with a nylon mesh hair net and applied barrier cream over the palms of her hands. She tanned in the coating chamber. The subject above was coated for 7 seconds. About 300 grams of solution was applied during such time. There was a subsequent 7 second period in which the mist was circulated in the booth. The residual mist was removed from the booth and the subject dried for about 45 seconds. The subject then removed any excess lotion with a towel. The final result was that the subject was 1 to 2 shades darker after tanning. This difference was especially apparent when comparing the area under the sticker with the area with no sticker. The initial color was mainly from the bronzer, and is a deep brown color. Color was much more intense the next day, when the color was at least two shades darker than before tanning. After the subject showered, the intensity was dropped to about 1 shade darker than prior to tanning. This color, which was mainly from the dihydroxyacetone, was golden brown. The color persisted about 1 shade darker for 3–4 days, and noticeable color was present for 7 days.

Example 2

A forty seven year old male with type II skin tanned by this process. He first applied a heart shaped sticker on his right arm. He covered his hair with a nylon mesh hair net and applied barrier cream over the palms of his hands and the bottoms of his feet. He tanned in the coating chamber. The subject above was coated for 7 seconds. About 300 grams of solution was applied during time. There was a subsequent 7 second period in which the mist was circulated in the booth. The residual mist was removed from the booth and the subject dried for about 45 seconds. The subject then removed any excess lotion with a towel. The final result was that the subject was about 1 shade darker after tanning. This difference was especially apparent when comparing the area under the sticker with the area with no sticker. The initial color was mainly from the bronzer, and is a deep brown color. Color was much more intense the next day, when the color was one to two shades darker than before tanning. After the subject showered, the intensity was dropped to about 1 shade darker than prior to tanning. This color, which was mainly from the dihydroxyacetone, was golden brown. The subject repeated the tanning process again later the second day. This time, the initial tan from the combination of previous tan and new bronzer was about 2 shades darker than before. Even after showering the next day, the tan was about two shades darker than prior to initially tanning. The color persisted about 2 shades darker for 3–4 days, and noticeable color was present for 10 days.

Example 3

A 24 year old female with type II skin tanned as described in examples 1 and 2 for five consecutive days. The results were a highly uniform, very dark tan. Her skin color was about 3 shades darker by the end of the week. The color was golden brown. The color remained 2 to 3 shades darker for about 4 days, and some color (about 1 shade) was observed after 7 days.

Discoveries

Very Fast Drying:

Traditional sunless tanning products require 20 minutes or more to dry. The sunless tanning composition of the present invention drys within a minute after use.

Less Transfer to Clothing Than Expected:

Traditional sunless tanning products do not contain bronzers because bronzers transfer to clothing and other fabrics. The present invention exhibits almost no such transfer.

Tan Hue Less Orange Than Expected:

The combination of bronzers, tan enhancers, and a super application process produces a long lasting, golden brown color.

Hair is not Turned Orange:

Self-tanning lotions have been reported to turn body hair orange. The formulation and application of the present invention do not cause the hair to turn orange. First, the formulation does not penetrate the hair, but rather beads up on it. Next, it is applied in a very thin coat. The net result is that the hair does not turn orange.

Produces a Very Uniform Tan:

The present invention facilitates the application of a thin, uniform film over the entire body. Streaking and spotting are rarely observed. Consequently, the resulting coating and tan is far superior to manual application methods.

Bronzer Tends to Last Longer Than Expected:

The bronzer provides immediate color and a method for observing the uniformity of the tan. The uniformity of the bronzer application is greatly enhanced because it is applied in a uniform thin film and its substantivity is enhanced because of deeper penetration into skin with the presence of a penetration enhancer.

Use of Ethoxy Diglycol as a Penetration Enhancer Makes the Tan Last Longer and More Uniform:

With the use of ethoxy diglycol, the duration of uniform intense tan has increased from an average of about 2 days to an average of about 4 days, and some color persists for up to 14 days.

Although preferred embodiments of the invention are illustrated in the Drawings and described in the Detailed Description, it will be understood that the invention is not limited to the embodiments disclosed, but is capable of numerous modifications and rearrangements of parts and elements without departing from the spirit of the invention.

What is claimed is:

1. An apparatus for coating substantially the entire human body including the head with a predetermined human skin coating material comprising:

structure defining a coating chamber for receiving the entire body including the head of a person to be coated;

at least one stationary mist generating nozzle mounted within the coating chamber for misting the predetermined human skin coating material onto the skin of the person in the coating chamber; and at least one air jet positional to direct a flow of air into engagement with the mist generated by the stationary mist generating nozzle for moving the mist generated by the nozzle relative to the body and the head of the person to be coated thereby assuring a uniform coating of the predetermined human skin coating material over substantially the entire body including the head of the person.

2. An apparatus for coating substantially the entire human body with a predetermined human skin coating material comprising:

structure defining a coating chamber for receiving the entire body of a person to be coated;

a plurality of stationary mist generating nozzles mounted within the coating chamber for misting the predetermined human skin coating liquid onto the skin of the person in the coating chamber; and a plurality of airs jet air jets each positioned to direct a flow of air into engagement with the mist generated by at least one the stationary mist generating nozzles for moving the mist generated by the nozzle relative to the body of the person to be coated thereby assuring a uniform coating of the predetermined human skin coating material over at least part of the body of the person.

3. The apparatus for coating the human body with a predetermined human skin coating material according to claim 2 further comprising:

a cannister for receiving the human skin coating material in liquid form; and apparatus for pressurizing the interior of the cannister and thereby discharging liquid from the cannister through the stationary mist generating nozzles.

4. The apparatus according to claim 3 further characterized by a fluid conduit extending from the cannister to the nozzles and a pressure regulator in the conduit, and further including a recirculation pump connected between a point in the fluid conduit closely adjacent the nozzles and a point in the conduit closely adjacent the pressure regulator.

5. The apparatus according to claim 4 further including a filter for removing particulate matter from the recirculating liquid.

6. The method for coating the human body according to claim 2 wherein the coating composition is a predetermined suntanning composition.

7. The method for coating the human body according to claim 2 wherein the coating composition is a predetermined tanning accelerator composition.

8. The method for coating the human body according to claim 2 wherein the coating composition is a predetermined sunburn treatment composition.

9. The method for coating the human body according to claim 2 wherein the coating composition is a predetermined insect repellant composition.

10. The method for coating the human body according to claim 2 wherein the coating composition is a predetermined skin toner composition.

11. The meted for coating the human body according to claim 2 wherein the coating composition is a predetermined skin bleach composition.

12. The method for coating the human body according to claim 2 wherein the coating composition is a predetermined skin lightening composition.

13. The method for coating the human body according to claim 2 wherein the coating composition is a predetermined anti-microbial composition.

14. The method for coating the human body according to claim 2 wherein the coating composition is a predetermined moisturizer composition.

15. The method for coating the human body according to claim 2 wherein the coating composition is a predetermined exfoliant composition.

16. The method for coating the human body according to claim 2 wherein the coating composition is a predetermined nutriment and vitamin composition.

17. The method for coating the human body according to claim 2 wherein the coating composition is a predetermined massaging aid composition.

18. The method for coating the human body according to claim 2 wherein the coating composition is a predetermined muscle relaxant composition.

19. The method for coating the human body according to claim 2 wherein the coating composition is a predetermined medicated skin treatment composition.

20. The method for coating the human body according to claim 2 wherein the coating composition is a predetermined burn treatment composition.

21. The method for coating the human body according to claim 2 wherein the coating composition is a predetermined decontamination composition.

22. The method for coating the human body according to claim 2 wherein the coating composition is a predetermined cosmetic composition.

23. The method for coating the human body according to claim 2 wherein the coating composition is a predetermined wrinkle treatment composition.

24. An apparatus for coating substantially the entire human body with a predetermined human skin self-tanning material comprising:
   structure defining a coating chamber for receiving the entire body of a person to be coated;
   a plurality of stationary mist generating nozzles mounted within the coating chamber for misting the predetermined human skin self-tanning material onto the skin of the person in the coating chamber; and
   a plurality of air jets each positioned to direct a flow of air into engagement with the mist generated by at least one of the stationary mist generating nozzles for moving the mist generated by the nozzle relative to the body of the person to be coated thereby assuring a uniform coating of the predetermined human skin self-tanning material over substantially the entire body of the person.

25. An apparatus for coating substantially the entire human body with a predetermined human skin coating material comprising:
   structure defining a coating chamber for receiving the entire body of a person to be coated;
   a plurality of stationary mist generating nozzles mounted within the coating chamber for misting the predetermined human skin coating material onto the skin of the person in the coating chamber; and
   a plurality of air jets each positioned to direct a flow of air into engagement with the mist generated by at least one of the stationary mist generating nozzles for moving the mist generated by the nozzle relative to the body of the person to be coated thereby assuring a uniform coating of the predetermined human skin coating material over substantially the entire body of the person;
   the stationary mist generating nozzles and their associated air jets being positioned at spaced apart locations around the body of a person within the coating chamber for coating substantially all areas of the body of the person simultaneously.

26. An apparatus for coating substantially the entire human body including the head with a predetermined human skin coating material comprising:
   structure defining a coating chamber for receiving the entire body including the head of a person to be coated;
   at least one stationary mist generating nozzle mounted within the coating chamber for misting the predetermined human skin coating material onto the skin of the person in the coating chamber; and
   at least one air jet for directing a flow of air into engagement with the mist generated by the nozzle and thereby moving the mist generated by the nozzle relative to the body and the head of the person to be coated thereby assuring a uniform coating of the predetermined human skin coating material over substantially the entire body including the head of the person.

* * * * *